United States Patent [19]
McKay et al.

[11] Patent Number: 5,459,072
[45] Date of Patent: Oct. 17, 1995

[54] FOOD-GRADE INTEGRATION VECTORS FOR INDUSTRIAL BACTERIAL STRAINS

[75] Inventors: Larry L. McKay, St. Paul, Minn.; Kayla M. Polzin, Ames, Iowa

[73] Assignee: Regents of the University of Minnesota, Minneapolis, Minn.

[21] Appl. No.: 220,958

[22] Filed: Mar. 31, 1994

Related U.S. Application Data

[63] Continuation of Ser. No. 841,642, Feb. 25, 1992, abandoned.
[51] Int. Cl.$^6$ .......................... C12N 15/00; C12N 15/63
[52] U.S. Cl. .................... 435/320.1; 435/172.3; 435/173.1; 435/173.6; 435/252.3
[58] Field of Search .......................... 435/320.1, 172.3, 435/69.1, 252.3–252.35, 173.1, 173.6

OTHER PUBLICATIONS

Boswell et al. (1988) In: Computational Molecular Biology, ed. Arthur M. Lesk, Oxford University Press, Oxford, N.Y., Tokyo: 161–178.
Froseth et al. (1991) Appl Environ. Microbio. vol. 57(3): 804–811.
Von Wright et al. (1990) Appl. Environ. Microbio. vol. 56(7): 2029–2035.
McKay et al. (1989) Appl. Environ. Microbio. vol. 55(10): 2702–2709.
Polzin et al. (1992) Applied Environ. Microbiol. vol. 58(2): 476–484.
Biswas et al., "High-Efficiency Gene Inactivation and Replacement System for Gram–Positive Bacteria", *J. Bacteriol.*, 175:3628–3635 (1993).
Harlander et al., "Molecular Cloning of the Lactose–Metabolizing Genes from *Streptococcus lactis*", *Appl. Environ. Microbiol.*, 48:347–351 (1984).
Kok et al., "Cloning and Expression of a *Streptococcus cremoris* Proteinase in *Bacillus subtilis* and *Streptococcus lactis*", *Appl. Environ. Microbiol.*, 50:94–101 (1985).
Laible et al., "Identification and Cloning of Plasmid Deoxyribonucleic Acid Coding for Abortive Phage Infeection from *Streptococcus lactis* ssp. *diacetylactis* KR2", *J. Dairy Sci.*, 70:2211–2219 (1987).
Maguin et al., "New Thermosensitive Plasmid for Gram–Positive Bacteria", *J. Bacteriol.*, 174:5633–5638 (1992).
McKay, "Application of Genetic Engineering Techniques for Dairy Starter Culture Improvement" Chapter 9 in *Biotechnology in Food Processing*, Susan Harlander and Theodore Labuza (editors), Noyes Publications, Park Ridge, N.J. at pp. 145–155 (1986).
Polzin et al., "Copy Number and Location of Insertion Sequences IS*S1* and IS*981* in Lactococci and Several Other Lactic Acid Bacteria", *J. Dairy Sci.*, 76:1243–1252 (1993).
Polzin et al., "Construction of a lactococcal integration vector using a lactococcal plasmid encoding temperature–sensitive maintenance", *J. Dairy Sci.*, 74(supp):121 Abstract D122 (1991).
J. Horng et al., "Replication and Temperature Sensitive Functions of Lactose Plasmid pSK11L from *Lactococcus lactis* subsp. *cremoris*", *J. Bact.*, 173:7573–7581 (1991).
L. Janniere et al., "Stable Gene Amplification in the Chromosome of *Bacillus subtilis*" *Gene*, 40:47–55 (1985).
P. Kallio et al., "Enhancement of Á–amylase Production by Integrating and Amplifying the Á–amylase Gene of *Bacillus amyloliquefaciens* in the Genome of *Bacillus subtilis*", *Appl. Microbiol. Biotech.*, 27:64–71 (1987).
K. Leenhouts et al., "Campbell–Like Integration of Hetrologous Plasmid DNA into the Chromosome of *Lactococcus lactis* subsp. *lactis*", *Appl. Environ. Microbiol.*, 55:394–400 (1989).
K. Leenhouts et al., "Stability of Integrated Plasmids in the Chromosome of *Lactococcus lactis*", *Appl. Environ. Microbiol.*, 56:2726–2735 (1990).
Larry L. McKay, "Genetic Modification of Lactococci for Improved Starter Performance", Abstract D30, *J. Dairy Science*, 73(Supp. 1):79 (1990).
K. Polzin et al., "Identification of a New Insertion Element, Similar to Gram–Negative IS26, on the Lactose Plasmid of *Streptococcus lactis* ML3", *J. Bacteriol.*, 16:5481–5488 (1987).
K. Polzin et al., "Identification, DNA Sequence, and Distribution of IS981, a New High–Copy–Number Insertion Sequence in Lactococci", *Appl. Env. Micro.*, 57:734–743 (1991).
Roberts et al., "Genetic Characterization of the Stabilizing Functions of a Region of Broad–Host–Range Plasmid RK2", *J. Bact.*, 172:6204 (1990).
D. Romero et al., "Characterization of Insertion Sequence IS946, and Iso–ISS1 Element, Isolated from the Conjugative Lactococcal Plasmid pTR2030", *J. Bact.*, 172:4151 (1990).

(List continued on next page.)

*Primary Examiner*—James Martinell
*Attorney, Agent, or Firm*—Merchant, Gould, Smith, Edell, Welter & Schmidt

[57] ABSTRACT

The present invention is directed to integration vectors including food-grade integration vectors, a method of increasing the stability of the inheritance of genes in microorganisms and transformed microorganisms containing an integrated vector and which exhibit an increase in the stability of inheritance of a gene. The integration vector is comprised of a first DNA sequence encoding a temperature sensitive plasmid maintenance and replication region, a second DNA sequence encoding at least one selectable marker gene, a third DNA sequence encoding an insertion sequence, and a fourth DNA sequence which encodes an unstable gene. The method of increasing the stability of the inheritance of a gene includes introducing the integration vector into a host microorganism, selecting transformed microorganisms, and confirming that selected microorganisms exhibit an increase in the stability of inheritance of a gene encoding a trait. Transformed microorganisms are provided which have at least one integration vector integrated into the genome and which exhibit an increase in the stability of the inheritance of a gene encoding a trait. The invention also provides DNA sequences substantially corresponding to a temperature sensitive plasmid maintenance and replication sequence, a nisin resistance gene, and a novel lactococcal insertion sequence.

28 Claims, 5 Drawing Sheets

OTHER PUBLICATIONS

D. Romero et al., "Conjugative Mobilization as an Alternative Vector Delivery System for Lactic Streptococci", *Appl. Environ. Microbiol.*, 53:2405 (1987).

D. Anderson et al., "Simple and Rapid Method for Isolating Large Plasmid DNA from Lactic Streptococci", *Appl. Environ. Microbiol.*, 46:549–553 (1983).

M. Chopin et al., "Insertion and Amplification of Foreign Genes in the *Lactococcus lactis* subsp. *lactis* Chromosome", *App. Environ. Microbiol.*, 55:1769–1774 (1989).

F. DeBrujin et al., "The Use of Transposon Tn5 Mutagenesis in the Rapid Generation of Correlated Physical and Genetic Maps of DNA Segments Cloned into Multicopy Plasmids–A Review", *Gene*, 27:131–149 (1984).

Feirtag et al., "Thermosensitive Plasmid Replication, Temperature Sensitive Host Growth, and Chromosomal Plasmid Integration Conferred by *Lactococcus lactis* subsp. *cremoris* Lactose Plasmids in *Lactococcus lactis* subsp. *lactis*", *J. Dairy Science*, 73 (Supplement 1), p. 72 (1990).

J. Feirtag et al., "Thermosensitive Plasmid Replication, Temperature–Sensitive Host Growth, and Chromosomal Plasmid Integration Conferred by *Lactococcus lactis* subsp. *cremoris* Lactose Plasmids in *Lactococcus lactis* subsp. *lactis*", *Appl. Environ. Microbiol.*, 57:539–548 (1991).

B. Froseth et al., "Molecular Characterization of the Nisin Resistance Region of *Lactococcus lactis* subsp. *lactis* Biovar Diacetylactis DRC3", *Appl. and Env. Micro.*, 57:804–811 (1991).

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1506 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( v i ) ORIGINAL SOURCE:
        ( A ) ORGANISM: Lactococcus lactis subsp cremoris
        ( B ) STRAIN: SK11

( v i i ) IMMEDIATE SOURCE:
        ( B ) CLONE: ORI Site/OPEN Reading Frame of Replication Region of PSK11L ( v i i i ) POSITION IN GENOME:
        ( C ) UNITS: bp ( i x ) FEATURE:
        ( A ) NAME/KEY: CDS
        ( B ) LOCATION: 345..1496

( x i ) SEQUENCE DESCRIPTION: SEQ ID NO:1:

```
ATCAGCTAAA   TCACTGGAAC   CAGAGACTTT   AAGATATTCT   ATCGGGTATC   AAGTCATGGC            60

TAAATAATCA   ACTAGCAATT   CGGGTATTTT   AAAAAAAGAA   AATTGGGACT   CCTTAGAGTC           120

CCTTTTAATT   ATTTTATATT   ATATATTTTG   TCTTTTGTTC   TTTTGCGAAA   AAAAAAATCT           180

AGTGTTTGCA   AGGGGTAACA   GGATTATAGT   CCTACAAAAA   ACTGTGCATA   GTCCTACAAA           240

AAACTGTGTA   TAGTCCTACA   AAAAACTGTG   TATAGTCCTA   CAAGTTATTT   GTGTTTGTAG           300

GTGTTTCGTG   TTATTATTTA   TTTAAATCAT   AAAAGGAGTG   GATT ATG CAA  AAG ATA            356
                                                       Met Gln  Lys Ile
                                                        1
```

| | | | | | | | | | | | | | | | | |
|---|---|---|---|---|---|---|---|---|---|---|---|---|---|---|---|---|
| GAC | ACA | GGA | GAA | AGA | AAT | AAA | CAA | ATA | CAG | GAA | ATA | AGT | TCA | AGG | AAG | 404 |
| Asp | Thr | Gly | Glu | Arg | Asn | Lys | Gln | Ile | Gln | Glu | Ile | Ser | Ser | Arg | Lys | |
| 5 | | | | 10 | | | | | 15 | | | | | | 20 | |
| GTG | GCA | GAG | CAT | AAC | GAT | TTA | ATT | AGC | TCA | GTT | GCA | AAA | ATG | GAT | AAG | 452 |
| Val | Ala | Glu | His | Asn | Asp | Leu | Ile | Ser | Ser | Val | Ala | Lys | Met | Asp | Lys | |
| | | | | 25 | | | | | 30 | | | | | 35 | | |
| ACA | CCA | TTA | AAA | ATG | TTT | GAG | CTA | GCT | GTT | TCA | TGT | ATA | GAT | ACT | GAT | 500 |
| Thr | Pro | Leu | Lys | Met | Phe | Glu | Leu | Ala | Val | Ser | Cys | Ile | Asp | Thr | Asp | |
| | | | 40 | | | | | 45 | | | | | 50 | | | |
| GCT | CCT | CCT | AAA | GAT | AAT | ATA | GTA | TTC | TTG | TCA | AAA | AAG | GAA | TTA | TTT | 548 |
| Ala | Pro | Pro | Lys | Asp | Asn | Ile | Val | Phe | Leu | Ser | Lys | Lys | Glu | Leu | Phe | |
| | | 55 | | | | | 60 | | | | | 65 | | | | |
| ACT | TTT | TTT | GAT | GTT | TCT | GAT | AAT | GAT | AAA | CAT | CGT | CGT | TTT | AAG | GAA | 596 |
| Thr | Phe | Phe | Asp | Val | Ser | Asp | Asn | Asp | Lys | His | Arg | Arg | Phe | Lys | Glu | |
| | | 70 | | | | | 75 | | | | | 80 | | | | |
| GCT | GTT | GAA | AAA | ATG | CAA | GAA | CAA | GCT | TTT | TTC | AGA | ATA | AAG | GAG | AAA | 644 |
| Ala | Val | Glu | Lys | Met | Gln | Glu | Gln | Ala | Phe | Phe | Arg | Ile | Lys | Glu | Lys | |
| 85 | | | | | 90 | | | | | 95 | | | | | 100 | |
| AAG | AAT | AGA | GGG | TTC | AAG | TTT | AAA | CGG | ATA | GTA | CCT | ATA | CCT | TAT | GTT | 692 |
| Lys | Asn | Arg | Gly | Phe | Lys | Phe | Lys | Arg | Ile | Val | Pro | Ile | Pro | Tyr | Val | |
| | | | | 105 | | | | | 110 | | | | | 115 | | |
| GAG | TGG | AAT | GAT | TAT | AAT | GAT | AAA | GTT | TTG | ATA | CGT | TTT | GAT | CAA | GCT | 740 |
| Glu | Trp | Asn | Asp | Tyr | Asn | Asp | Lys | Val | Leu | Ile | Arg | Phe | Asp | Gln | Ala | |
| | | | 120 | | | | | 125 | | | | | 130 | | | |
| ATT | ATG | CCT | TAT | CTC | ATA | GAT | TTA | AAA | AAT | AAT | TTT | ACG | CAA | TAT | GCC | 788 |
| Ile | Met | Pro | Tyr | Leu | Ile | Asp | Leu | Lys | Asn | Asn | Phe | Thr | Gln | Tyr | Ala | |
| | | 135 | | | | | 140 | | | | | 145 | | | | |
| ATA | TCA | GAT | ATT | ATG | GAA | CTG | AAT | AGC | AAG | TAC | AGT | ATT | ATT | TTA | TAT | 836 |
| Ile | Ser | Asp | Ile | Met | Glu | Leu | Asn | Ser | Lys | Tyr | Ser | Ile | Ile | Leu | Tyr | |
| | 150 | | | | | 155 | | | | | 160 | | | | | |
| AAA | TGG | TTC | TCT | ATG | TCT | TAT | AAT | CAA | TTT | GAG | CAT | TAC | CAA | TAT | AAA | 884 |
| Lys | Trp | Phe | Ser | Met | Ser | Tyr | Asn | Gln | Phe | Glu | His | Tyr | Gln | Tyr | Lys | |
| 165 | | | | | 170 | | | | | 175 | | | | | 180 | |
| CCT | AAT | AGA | ACG | AAG | AAA | CAA | TTG | GAA | GAT | TAC | AAG | AGT | CCT | AGG | ATA | 932 |
| Pro | Asn | Arg | Thr | Lys | Lys | Gln | Leu | Glu | Asp | Tyr | Lys | Ser | Pro | Arg | Ile | |
| | | | | 185 | | | | | 190 | | | | | 195 | | |
| ATA | ATT | AGT | GAC | TTA | AGA | GAA | TTA | ACA | GAT | ACT | GTT | GAT | GAC | TAT | AGT | 980 |
| Ile | Ile | Ser | Asp | Leu | Arg | Glu | Leu | Thr | Asp | Thr | Val | Asp | Asp | Tyr | Ser | |
| | | | 200 | | | | | 205 | | | | | 210 | | | |
| AGA | TTT | GAT | AAT | TTT | GAA | AAA | AGA | GTC | ATA | AAA | GAT | GCA | ATT | AAA | GAA | 1028 |
| Arg | Phe | Asp | Asn | Phe | Glu | Lys | Arg | Val | Ile | Lys | Asp | Ala | Ile | Lys | Glu | |
| | | | 215 | | | | | 220 | | | | | 225 | | | |
| ATA | AAT | TCT | TTT | ACT | CAT | TTT | AAT | GTT | GAG | TAT | AAA | AAA | ATA | AAA | AAA | 1076 |
| Ile | Asn | Ser | Phe | Thr | His | Phe | Asn | Val | Glu | Tyr | Lys | Lys | Ile | Lys | Lys | |
| | | 230 | | | | | 235 | | | | | 240 | | | | |
| GGA | CGT | TCA | ATC | GAT | TCA | ATA | CAG | TTT | CAT | ATA | GTT | AAG | AAA | GCA | AAT | 1124 |
| Gly | Arg | Ser | Ile | Asp | Ser | Ile | Gln | Phe | His | Ile | Val | Lys | Lys | Ala | Asn | |
| 245 | | | | 250 | | | | | 255 | | | | | 260 | | |
| TGG | AAA | GAT | GAG | AAC | TAT | AAA | CGT | AAT | GAT | GTA | CAA | GCA | CAA | TTA | ACT | 1172 |
| Trp | Lys | Asp | Glu | Asn | Tyr | Lys | Arg | Asn | Asp | Val | Gln | Ala | Gln | Leu | Thr | |
| | | | | 265 | | | | | 270 | | | | | 275 | | |
| GAA | GAA | CAA | AAT | CAA | GCT | CAA | AAT | CAG | GTT | AAT | TAT | GCA | GTA | GCA | GTT | 1220 |
| Glu | Glu | Gln | Asn | Gln | Ala | Gln | Asn | Gln | Val | Asn | Tyr | Ala | Val | Ala | Val | |
| | | | 280 | | | | | 285 | | | | | 290 | | | |
| GCA | AAT | CCT | TTT | ACC | ATG | AAA | CTT | ATA | AAT | TCC | TCT | TTG | TAT | GCA | | 1268 |
| Ala | Asn | Pro | Phe | Thr | Met | Lys | Leu | Ile | Asn | Ser | Ser | Leu | Leu | Tyr | Ala | |
| | | 295 | | | | | 300 | | | | | 305 | | | | |
| ACT | GAT | ATA | GCA | AAC | CAG | GAC | ACG | ATT | TTA | GAG | CTT | GCT | GAG | AGT | GTT | 1316 |
| Thr | Asp | Ile | Ala | Asn | Gln | Asp | Thr | Ile | Leu | Glu | Leu | Ala | Glu | Ser | Val | |

```
              310                    315                        320
TAT  CCT  GTG  TAT  GAT  AAA  CTT  GTA  AAA  GAA  CTC  GGA  GAA  GAT  GCC  TTA   1364
Tyr  Pro  Val  Tyr  Asp  Lys  Leu  Val  Lys  Glu  Leu  Gly  Glu  Asp  Ala  Leu
325                 330                      335                      340

GAA  ACG  CAT  ATG  GAC  TAT  GTA  CGA  AGA  AAG  ATG  GTA  GAT  TAT  TCA  AAT   1412
Glu  Thr  His  Met  Asp  Tyr  Val  Arg  Arg  Lys  Met  Val  Asp  Tyr  Ser  Asn
                    345                      350                      355

GAT  AAA  AAG  AAT  ATC  GTA  AAG  TAT  TTA  AGT  ATA  TCA  GCA  AAA  CAA  TAT   1460
Asp  Lys  Lys  Asn  Ile  Val  Lys  Tyr  Leu  Ser  Ile  Ser  Ala  Lys  Gln  Tyr
               360                      365                      370

CTT  AAT  TCA  AGG  TTG  AGT  AAA  CAG  CAA  ATG  AAA  GAG  TAAGGAAGAA            1506
Leu  Asn  Ser  Arg  Leu  Ser  Lys  Gln  Gln  Met  Lys  Glu
          375                      380
```

( 2 ) INFORMATION FOR SEQ ID NO:2:

( i ) SEQUENCE CHARACTERISTICS:
        ( A ) LENGTH: 384 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Gln  Lys  Ile  Asp  Thr  Gly  Glu  Arg  Asn  Lys  Gln  Ile  Gln  Glu  Ile
 1                  5                        10                      15

Ser  Ser  Arg  Lys  Val  Ala  Glu  His  Asn  Asp  Leu  Ile  Ser  Ser  Val  Ala
               20                       25                      30

Lys  Met  Asp  Lys  Thr  Pro  Leu  Lys  Met  Phe  Glu  Leu  Ala  Val  Ser  Cys
               35                       40                      45

Ile  Asp  Thr  Asp  Ala  Pro  Pro  Lys  Asp  Asn  Ile  Val  Phe  Leu  Ser  Lys
          50                       55                      60

Lys  Glu  Leu  Phe  Thr  Phe  Phe  Asp  Val  Ser  Asp  Asn  Asp  Lys  His  Arg
 65                      70                      75                      80

Arg  Phe  Lys  Glu  Ala  Val  Glu  Lys  Met  Gln  Glu  Gln  Ala  Phe  Phe  Arg
                    85                       90                      95

Ile  Lys  Glu  Lys  Lys  Asn  Arg  Gly  Phe  Lys  Phe  Lys  Arg  Ile  Val  Pro
               100                      105                     110

Ile  Pro  Tyr  Val  Glu  Trp  Asn  Asp  Tyr  Asn  Asp  Lys  Val  Leu  Ile  Arg
          115                      120                     125

Phe  Asp  Gln  Ala  Ile  Met  Pro  Tyr  Leu  Ile  Asp  Leu  Lys  Asn  Asn  Phe
     130                      135                     140

Thr  Gln  Tyr  Ala  Ile  Ser  Asp  Ile  Met  Glu  Leu  Asn  Ser  Lys  Tyr  Ser
145                      150                      155                     160

Ile  Ile  Leu  Tyr  Lys  Trp  Phe  Ser  Met  Ser  Tyr  Asn  Gln  Phe  Glu  His
               165                      170                     175

Tyr  Gln  Tyr  Lys  Pro  Asn  Arg  Thr  Lys  Lys  Gln  Leu  Glu  Asp  Tyr  Lys
               180                      185                     190

Ser  Pro  Arg  Ile  Ile  Ile  Ser  Asp  Leu  Arg  Glu  Leu  Thr  Asp  Thr  Val
          195                      200                     205

Asp  Asp  Tyr  Ser  Arg  Phe  Asp  Asn  Phe  Glu  Lys  Arg  Val  Ile  Lys  Asp
     210                      215                     220

Ala  Ile  Lys  Glu  Ile  Asn  Ser  Phe  Thr  His  Phe  Asn  Val  Glu  Tyr  Lys
225                      230                      235                     240

Lys  Ile  Lys  Lys  Gly  Arg  Ser  Ile  Asp  Ser  Ile  Gln  Phe  His  Ile  Val
               245                      250                     255

Lys  Lys  Ala  Asn  Trp  Lys  Asp  Glu  Asn  Tyr  Lys  Arg  Asn  Asp  Val  Gln
```

|   | 260 |   |   |   | 265 |   |   |   | 270 |   |   |
|---|---|---|---|---|---|---|---|---|---|---|---|

Ala Gln Leu Thr Glu Glu Gln Asn Gln Ala Gln Asn Gln Val Asn Tyr
            275                 280                 285

Ala Val Ala Val Ala Asn Pro Phe Thr Met Lys Leu Ile Asn Ser Ser
        290                 295                 300

Leu Leu Tyr Ala Thr Asp Ile Ala Asn Gln Asp Thr Ile Leu Glu Leu
305                     310                 315                 320

Ala Glu Ser Val Tyr Pro Val Tyr Asp Lys Leu Val Lys Glu Leu Gly
                325                 330                 335

Glu Asp Ala Leu Glu Thr His Met Asp Tyr Val Arg Arg Lys Met Val
            340                 345                 350

Asp Tyr Ser Asn Asp Lys Lys Asn Ile Val Lys Tyr Leu Ser Ile Ser
        355                 360                 365

Ala Lys Gln Tyr Leu Asn Ser Arg Leu Ser Lys Gln Gln Met Lys Glu
    370                 375                 380

( 2 ) INFORMATION FOR SEQ ID NO:3:

( i ) SEQUENCE CHARACTERISTICS:
    ( A ) LENGTH: 1454 base pairs
    ( B ) TYPE: nucleic acid
    ( C ) STRANDEDNESS: single
    ( D ) TOPOLOGY: linear ( i i ) MOLECULE TYPE: DNA (genomic)

( i v ) ANTI-SENSE: NO ( v i ) ORIGINAL SOURCE:
    ( A ) ORGANISM: Lactococcus lactis subsp lactis bv.
      diacetylactis
    ( B ) STRAIN: DRC3

( v i i ) IMMEDIATE SOURCE:
    ( B ) CLONE: Nisin Resistance Gene and Flanking Regions ( i x ) FEATURE:
    ( A ) NAME/KEY: CDS
    ( B ) LOCATION: 354..1307

( x i ) SEQUENCE DESCRIPTION: SEQ ID NO:3:

```
GAATTCCTAG  TTGATTATTT  AGCCATGACT  TGATACCCGA  TAGAATATCT  TAAAGTCTCT        60

GGTTCCAGTG  ATTTAGCTGA  TTTTAACAGT  AAATAATACG  CTAAAAGTAT  CATCTCTAAT       120

TTCAATTGAA  AACCTTGAGG  CGAACGACTT  TTACAACGCT  CAGCTCCTAG  ATTTGTCAAA       180

AAATAGAAAA  CTAGTCATAA  CTTCCCATTA  TGTCTAATTT  TTAAACTTTG  AGTTAATATG       240

AGAGCGCAAA  ATTACTTCCT  AGATTTATCG  TTTACAATCA  GTCCAAAGTT  GCAGGATTTT       300

CCATTCAAAT  TATGTTTTAA  TAGTATTAAA  ATAACTGATG  GAGCATATTT  AAT ATG          356
                                                               Met
                                                                 1
```

AAA ATA GGT AAG CGC ATT TTA TTA GGT CTA GTG GCA GTA TGT GCT TTA  404
Lys Ile Gly Lys Arg Ile Leu Leu Gly Leu Val Ala Val Cys Ala Leu
            5                   10                  15

TTT TTA GGA ATT ATC TAT CTT TGG GGG TAT AAA TTC AAC ATA TAT TTA  452
Phe Leu Gly Ile Ile Tyr Leu Trp Gly Tyr Lys Phe Asn Ile Tyr Leu
        20                  25                  30

GTA CCA CCC TCC CCT CAG AAG TAT GTT CGA GTT GCC TTA AAA AAT ATG  500
Val Pro Pro Ser Pro Gln Lys Tyr Val Arg Val Ala Leu Lys Asn Met
    35                  40                  45

GAT GAA CTT GGG CTA TTT ACT GAT TCA AAA GAA TGG GTA GAA ACT AAA  548
Asp Glu Leu Gly Leu Phe Thr Asp Ser Lys Glu Trp Val Glu Thr Lys
50                  55                  60                  65

| | | | | | | | | | | | | | | | | |
|---|---|---|---|---|---|---|---|---|---|---|---|---|---|---|---|---|
| AAA | AAG | ACG | ATA | GAA | GAA | ACA | TCA | AAT | GCT | AAA | AAC | TAT | GCA | GAA | ACA | 596 |
| Lys | Lys | Thr | Ile | Glu 70 | Glu | Thr | Ser | Asn | Ala 75 | Lys | Asn | Tyr | Ala | Glu 80 | Thr | |
| ATC | CCT | TTT | TTA | CAA | AAA | GCG | ATT | AAA | GTT | GCA | GGA | GGA | AAG | CAT | TCT | 644 |
| Ile | Pro | Phe | Leu 85 | Gln | Lys | Ala | Ile | Lys 90 | Val | Ala | Gly | Gly | Lys 95 | His | Ser | |
| TTT | ATT | GAA | CAT | GAA | GAA | GAC | ATA | TCA | AAA | AGA | AGC | ATG | ACA | AAA | TAT | 692 |
| Phe | Ile | Glu 100 | His | Glu | Glu | Asp | Ile | Ser 105 | Lys | Arg | Ser | Met | Thr 110 | Lys | Tyr | |
| ATA | AAA | CCA | AAG | GCA | GAA | ATC | GAA | GGC | AAC | ACT | TTA | ATA | TTA | ACT | ATT | 740 |
| Ile | Lys 115 | Pro | Lys | Ala | Glu | Ile 120 | Glu | Gly | Asn | Thr | Leu 125 | Ile | Leu | Thr | Ile | |
| CCT | GAA | TTT | ACT | GGA | AAT | GAT | AGT | CAA | GCA | TCT | GAT | TAC | GCT | AAT | TTT | 788 |
| Pro 130 | Glu | Phe | Thr | Gly | Asn 135 | Asp | Ser | Gln | Ala | Ser 140 | Asp | Tyr | Ala | Asn | Phe 145 | |
| TTA | GAA | TCT | TCA | TTG | CAT | AAA | AAC | AAT | TAT | AAT | GGG | GTA | ATT | GTT | GAT | 836 |
| Leu | Glu | Ser | Ser | Leu 150 | His | Lys | Asn | Asn | Tyr 155 | Asn | Gly | Val | Ile | Val 160 | Asp | |
| TTG | AGG | GGG | AAT | AGA | GGT | GGA | GAC | TTA | TCT | CCT | ATG | GTA | TTA | GGA | TTA | 884 |
| Leu | Arg | Gly | Asn 165 | Arg | Gly | Gly | Asp | Leu 170 | Ser | Pro | Met | Val | Leu 175 | Gly | Leu | |
| TCC | CCC | CTA | TTG | CCT | GAT | GGA | ACT | CTA | TTT | ACT | TAT | GTT | GAT | AAA | AGT | 932 |
| Ser | Pro | Leu 180 | Leu | Pro | Asp | Gly | Thr 185 | Leu | Phe | Thr | Tyr | Val 190 | Asp | Lys | Ser | |
| AGT | CAT | TCT | AAA | CCT | GTT | GAA | CTA | CAA | AAT | GGA | GAA | ATA | AAT | AGT | GGC | 980 |
| Ser | His 195 | Ser | Lys | Pro | Val | Glu 200 | Leu | Gln | Asn | Gly | Glu 205 | Ile | Asn | Ser | Gly | |
| GGG | TCA | TCA | ACA | AAA | ATA | AGT | GAT | AAT | AAA | AAA | ATT | AAA | AAA | GCT | CCT | 1028 |
| Gly 210 | Ser | Ser | Thr | Lys | Ile 215 | Ser | Asp | Asn | Lys | Lys 220 | Ile | Lys | Lys | Ala | Pro 225 | |
| ATT | GCT | GTA | TTA | ATA | GAT | AAT | AAT | ACA | GGG | AGC | TCC | GGC | GAA | TTA | ACC | 1076 |
| Ile | Ala | Val | Leu | Ile 230 | Asp | Asn | Asn | Thr | Gly 235 | Ser | Ser | Gly | Glu | Leu 240 | Thr | |
| GCT | TTG | TGC | TTT | GAG | GGA | ATA | CCT | AAT | GTT | AAA | TTT | TTG | GGT | TCT | GAT | 1124 |
| Ala | Leu | Cys | Phe 245 | Glu | Gly | Ile | Pro | Asn 250 | Val | Lys | Phe | Leu | Gly 255 | Ser | Asp | |
| TCA | GCA | GGT | TAT | ACT | TCT | GCT | AAT | CAA | ACC | GTC | TAT | TTA | TAT | GAT | GGC | 1172 |
| Ser | Ala | Gly 260 | Tyr | Thr | Ser | Ala | Asn 265 | Gln | Thr | Val | Tyr | Leu 270 | Tyr | Asp | Gly | |
| TCA | ACA | TTA | CAA | ATA | ACT | TCT | GCT | TTT | GTA | AAA | GAC | AGA | ACA | AAT | AAT | 1220 |
| Ser | Thr 275 | Leu | Gln | Ile | Thr | Ser 280 | Ala | Phe | Val | Lys | Asp 285 | Arg | Thr | Asn | Asn | |
| ATT | TAT | AAA | AAT | TTT | CCT | ATT | AGT | CCG | GAC | ATT | CAA | ACA | AAT | AAT | GCT | 1268 |
| Ile 290 | Tyr | Lys | Asn | Phe | Pro 295 | Ile | Ser | Pro | Asp | Ile 300 | Gln | Thr | Asn | Asn | Ala 305 | |
| AAA | AGT | TCT | GCA | ATA | GAA | TGG | ATA | AAA | TCT | CAA | ATA | AAG | TAAAGCAAAA | | | 1317 |
| Lys | Ser | Ser | Ala | Ile 310 | Glu | Trp | Ile | Lys | Ser 315 | Gln | Ile | Lys | | | | |

| | | | | |
|---|---|---|---|---|
| AGACTTGCCA | AGAAAAACAT | ATGGTAAGTC | TTTTTTGCTA | GTCAAAACTT AACGTTATTT | 1377 |
| ACTATGATAT | ACCGAAAGCA | AGTACCAATG | CAGGTAAAAT | GTTGTTTAAA AGTGTATAGC | 1437 |
| TATACTACTC | TATCGTC | | | | 1454 |

( 2 ) INFORMATION FOR SEQ ID NO:4:

( i ) SEQUENCE CHARACTERISTICS:
        ( A ) LENGTH: 318 amino acids
        ( B ) TYPE: amino acid
        ( D ) TOPOLOGY: linear ( i i ) MOLECULE TYPE: peptide ( i i i ) HYPOTHETICAL: YES ( v i ) ORIGINAL SOURCE:
    ( A ) ORGANISM: Lactococcus lactis subsp lactis bv. diacetylactis
    ( B ) STRAIN: DRC3

( v i i ) IMMEDIATE SOURCE:
    ( B ) CLONE: Putative Nisin Resistance Gene ( x i ) SEQUENCE DESCRIPTION: SEQ ID NO:4:

```
Met Lys Ile Gly Lys Arg Ile Leu Leu Gly Leu Val Ala Val Cys Ala
 1               5                  10                  15

Leu Phe Leu Gly Ile Ile Tyr Leu Trp Gly Tyr Lys Phe Asn Ile Tyr
            20                  25                  30

Leu Val Pro Pro Ser Pro Gln Lys Tyr Val Arg Val Ala Leu Lys Asn
        35                  40                  45

Met Asp Glu Leu Gly Leu Phe Thr Asp Ser Lys Glu Trp Val Glu Thr
    50                  55                  60

Lys Lys Lys Thr Ile Glu Glu Thr Ser Asn Ala Lys Asn Tyr Ala Glu
65                  70                  75                  80

Thr Ile Pro Phe Leu Gln Lys Ala Ile Lys Val Ala Gly Gly Lys His
                85                  90                  95

Ser Phe Ile Glu His Glu Glu Asp Ile Ser Lys Arg Ser Met Thr Lys
            100                 105                 110

Tyr Ile Lys Pro Lys Ala Glu Ile Glu Gly Asn Thr Leu Ile Leu Thr
        115                 120                 125

Ile Pro Glu Phe Thr Gly Asn Asp Ser Gln Ala Ser Asp Tyr Ala Asn
    130                 135                 140

Phe Leu Glu Ser Ser Leu His Lys Asn Asn Tyr Asn Gly Val Ile Val
145                 150                 155                 160

Asp Leu Arg Gly Asn Arg Gly Gly Asp Leu Ser Pro Met Val Leu Gly
                165                 170                 175

Leu Ser Pro Leu Leu Pro Asp Gly Thr Leu Phe Thr Tyr Val Asp Lys
            180                 185                 190

Ser Ser His Ser Lys Pro Val Glu Leu Gln Asn Gly Glu Ile Asn Ser
        195                 200                 205

Gly Gly Ser Ser Thr Lys Ile Ser Asp Asn Lys Lys Ile Lys Lys Ala
    210                 215                 220

Pro Ile Ala Val Leu Ile Asp Asn Asn Thr Gly Ser Ser Gly Glu Leu
225                 230                 235                 240

Thr Ala Leu Cys Phe Glu Gly Ile Pro Asn Val Lys Phe Leu Gly Ser
                245                 250                 255

Asp Ser Ala Gly Tyr Thr Ser Ala Asn Gln Thr Val Tyr Leu Tyr Asp
            260                 265                 270

Gly Ser Thr Leu Gln Ile Thr Ser Ala Phe Val Lys Asp Arg Thr Asn
        275                 280                 285

Asn Ile Tyr Lys Asn Phe Pro Ile Ser Pro Asp Ile Gln Thr Asn Asn
    290                 295                 300

Ala Lys Ser Ser Ala Ile Glu Trp Ile Lys Ser Gln Ile Lys
305                 310                 315
```

( 2 ) INFORMATION FOR SEQ ID NO:5:

( i ) SEQUENCE CHARACTERISTICS:
        ( A ) LENGTH: 1222 base pairs ( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Lactococcus lactis
( B ) STRAIN: GBK17

( v i i ) IMMEDIATE SOURCE:
( B ) CLONE: IS981

( x i ) SEQUENCE DESCRIPTION: SEQ ID NO:5:

| | | | | | |
|---|---|---|---|---|---|
| GATGTTATCC | TTAAATCTTA | GAGTCACTAT | TGTATAATTT | AGACAAAGGA | CAAAAACATG | 60 |
| CAAAAACGCT | ACTCAAAAGA | ATTTAAAGAA | ACCCTTATCG | CCTTCTATCA | TTCTGGTCAA | 120 |
| TCCGTCACCC | AGCTGTCTAA | AGAATATGAC | GTGGCCCCTG | CAACAATTTA | TAAATGGATA | 180 |
| GACCTCTACT | CTAAATCTAA | TGAAAGCTCC | GTCTCTAAAG | CTGATTTTCT | AGAATTAAAA | 240 |
| AGACAACTGG | CTAAAGTTAA | GGAAGAACGA | GACATCTTAA | AAAAAGTATT | GACCATATTC | 300 |
| GCCGAGAAAA | AGAAGTGAGT | GCTGCGGATA | TGGCTCAAAC | CATACAAACT | TTAGCACTCA | 360 |
| ATGTCAGACT | AAGCTGTCAA | CTCCTTGATG | TTCCTGAATC | AAGTTATTAT | GAACGGATTA | 420 |
| ACCGACACCC | ATCTAAAACT | CAATTAAGGA | GACAATACCT | GTCACTCAAA | ATTTCTCAAC | 480 |
| TCTTCAATGC | TAACCGAGGA | ATCTATGGTG | CTCCTAAAAT | TCATCATCTT | CTACTTAAAC | 540 |
| AAGGGGAAAA | AGTCGGGTTA | AAACTGGTAC | AGAAGCTAAT | GAAGCAACTT | CAACTCAAGT | 600 |
| CTGTAGTCAT | TAAGAAATTT | AAGCCTGGAT | ACTCACTAAG | TGATCACATC | AATCGAAAAA | 660 |
| ATCTCATACA | GACTGAACCT | ACAAAGAAAA | ATAAGGTTTG | GTCAACCGAC | ATTACTTATA | 720 |
| TTCCTACTCA | ACAAGGATGG | GCTTATCTCT | CAACCATTAT | GGATCGTTAT | ACTAAAAAAG | 780 |
| TCATTGCTTG | GGATTTGGGC | AAGCGAATGA | CTGTAGAATT | AGTGCAAAGA | ACTTTAAATA | 840 |
| AGGCCATTAA | ATCACAAGAC | TATCCAGAAG | CTGTTATTCT | TCATTCTGAC | CAAGGAAGCC | 900 |
| AGTATACGAG | TCTAGAGTAT | GAAGAGTTGC | TTAAGTATTA | TGGGATGACT | CACTCTTTCA | 960 |
| GTCGAAGGGG | ATACCCTTAT | CATAATGCCA | GTCTTGAATC | TTGGCATGGA | CATTTAAAAA | 1020 |
| GAGAGTGGGT | GTACCAATTT | AAATATAAGA | ACTTTGAAGA | AGCCTATCAG | AGTATTTTCT | 1080 |
| GGTACATCGA | AGCCTTTTAT | AATTCAAAAC | GAATCCATCA | AAGTTTAGGG | TATCTTACAC | 1140 |
| CTAATCAATT | TGAAAAGGTA | AGTGCTTAAA | ATAAATAGAT | TAAAATTCTA | CGTTTGTTAC | 1200 |
| TCTAAAAACT | TGACTTAACG | TC | | | | 1222 |

FOOD-GRADE INTEGRATION VECTORS FOR INDUSTRIAL BACTERIAL STRAINS

This application is a continuation application of U.S. application Ser. No. 07/841,642 filed Feb. 25, 1992, now abandoned.

BACKGROUND OF THE INVENTION

Industrial strains of bacteria are used in the production of many food products including yogurt, sour cream, cheese, sausage, and sauerkraut. Bacterial strains which exhibit stable characteristics are essential to maintaining the flavor of the food product, the texture of the food product, and the quality of food product produced. An example of a bacterial genus of importance to the food industry is Lactococcus, strains of which carry out dairy fermentations by fermentation of lactose and degradation of milk proteins.

The proteins and enzymes involved in the fermentation and degradative pathways, as well as other desirable traits, are often encoded on plasmids. In some bacterial strains, these plasmids are easily lost resulting in bacterial strains with unstable characteristics and inconsistency in the quality, flavor, and type of food product produced by the strain. This problem is exacerbated when food production is scaled up and loss of desireable traits or characteristics of the bacteria causes the loss of the desirable fermentative properties and formation of an inferior and/or unacceptable food product.

One way plasmid encoded genetic traits or characteristics can be stabilized is by integration of an integration vector like a plasmid or a virus into the chromosome of the bacteria. Integration of vector genetic material into the bacterial chromosome can occur by recombination of the vector genetic material at a homologous site on the bacterial chromosome in a single or double crossover event. A single crossover event results in integration of the entire vector. Double crossover events result in incorporation of a portion of the vector genetic material. Once the vector genetic material is integrated into the chromosome, it is replicated as a part of the chromosome and the associated traits can be stably maintained for numerous generations.

Integration vectors have been used as genetic tools in a number of different bacteria. Vectors have been designed to delete chromosomal genes, to exchange wild type genes with mutated genes generated in vitro, to map chromosomal genes, to determine complementation and dominance, to generate in vivo gene fusions for transcriptional studies, to insert genes into conjugal transposons for transfer to non-transformable strains, to clone chromosomal genes, and to stabilize essential genes in industrially important microorganisms. An example of the use of integration vectors in the stabilization of essential genes is the integration of α-amylase genes from one species of Bacillus into the chromosome of another species of Bacillus by a nonreplicating vector containing random Bacillus chromosome fragments as reported by P. Kallio et al. in *Appl. Microbiol. Biotech.*, 27:64–71 (1987). The α-amylase gene was stably integrated, amplified and expressed in the Bacillus species.

The usefulness of integration vectors for transforming industrial bacterial strains depends upon the stability of the integrated sequences in the chromosome. The stability of the integrated plasmids is influenced by the type of crossover event which results in integration and on the type of vector. Vectors, such as RCR plasmids, whose retention of residual replication ability stimulate recombination and excision of the vector genetic material integrated by single crossover recombination, are not stably integrated. In contrast, non-RCR plasmids which integrate by single crossover events, with or without gene amplification, remain stably integrated in Bacillus as reported by L. Janniere et al. in *Gene*, 40:47–55 (1985).

Nonfood-grade vectors have been constructed, like for example, by insertion of antibiotic resistant marker genes and lactococcal chromosomal DNA into a non-lactococcal plasmid which cannot replicate in Lactococcus species. Several nonfood-grade lactococcal integration vectors have been studied, with varying abilities to provide stable integration into lactococcal species. K. Leenhouts et al., in *Appl. Environ. Microbiol.*, 56:2726 (1990), describe derivatives of plasmids from *E. coli* and *Saphylococcus aureas* which contain lactococcal chromosomal DNA and an erythromycin resistance gene that were capable of integrating into the chromosome of a strain of *Lactococcus lactis*. These results indicate great promise for stabilizing genes with integration vectors in bacterial strains of industrial importance.

In order for integration vectors to be currently applied in industrial processes to stabilize desireable genetic traits, the integration vector must be a food-grade vector. Food-grade vectors are considered acceptable for use in bacteria to be consumed by humans. To be food grade, the vectors are constructed of DNA corresponding to DNA sequences derived from microorganisms used in food and dairy fermentations, do not require passage through another microorganism not used in food or dairy fermentation, and contain a food-grade selectable marker gene. As described previously, currently available integration vectors are not food-grade because either they contain DNA from another non-food related genus of bacteria or they must be passed or amplified in another genus of bacteria or they lack a food-grade selectable marker gene. The two major obstacles for development of stable food-grade integration vectors have been the lack of easily selectable food-grade marker genes and the lack of conditionally maintained plasmids from which to construct integration vectors.

Accordingly, there is a need to develop food-grade integration vectors containing easily selectable food-grade marker genes. There is also a need to identify vectors which are composed of genetic material from strains of industrial bacteria to serve as food-grade integration vectors and which do not require passage through another type of bacterial host. There is also a need to develop industrial strains of bacteria that have stably integrated industrially valuable characteristics or traits, including fermentation of lactose and degradation of milk proteins.

SUMMARY OF THE INVENTION

The present invention is directed to integration vectors including food-grade integration vectors, and DNA sequences encoding a food-grade selectable marker gene, temperature sensitive plasmid replication and maintenance sequences and insertion sequences. The invention also provides a method of increasing the stability of the inheritance of genes in a microorganism and for transformed microorganisms with the integration vector integrated into the genome and which exhibit an increase in the stability of the inheritance of a gene encoding a trait.

The integration vectors of the invention are comprised of four DNA sequences operably joined together. The first DNA sequence encodes a microorganism plasmid replication sequence and a plasmid maintenance sequence. The plasmid maintenance sequence provides for temperature sensitive loss of autonomously replicating or unintegrated plasmids. The second DNA sequence encodes at least one selectable marker gene, preferably a food-grade marker gene. The third DNA sequence encodes a fragment of an insertion sequence which is substantially homologous to DNA sequences on the microorganism's genome. The fourth DNA sequence encodes at least one gene encoding a trait which is unstable. The integration vector is preferably a food-grade grade integration vector which is less than about 100 kb. The integration vector is also preferably further comprised of additional plasmid DNA.

DNA sequences substantially corresponding to a food-grade selectable marker gene, temperature sensitive bacterial plasmid replication and maintenance sequences, and a novel lactococcal insertion sequence are also provided by the invention.

The integration vectors are used in a method to increase the stability of the inheritance of genes encoding traits in a microorganism by integration of the vector carrying such genes into the microorganism's genome. The method includes introducing an integration vector comprised of a first DNA sequence encoding a plasmid replication and maintenance sequence, a second DNA sequence encoding at least one selectable marker gene, a third DNA sequence encoding a fragment of an insertion sequence, and a fourth DNA sequence encoding a gene for a trait which is unstable into a microorganism to form a transformed microorganism. The transformed microorganisms are subjected to a selective condition to provide for selection of a population of microorganisms which exhibit an increase in the stability of the inheritance of a gene encoding a trait. The selected population of microorganisms is then grown through a plurality of growth cycles to confirm that a population of microorganisms which exhibit an increase in the stability of inheritance of a gene encoding a trait is confirmed. Accordingly, the invention also provides for transformed microorganisms with the integration vector integrated into the genome and which exhibit an increase in the stability of inheritance of a gene encoding a trait.

DETAILED DESCRIPTION OF THE INVENTION

Figure 1:
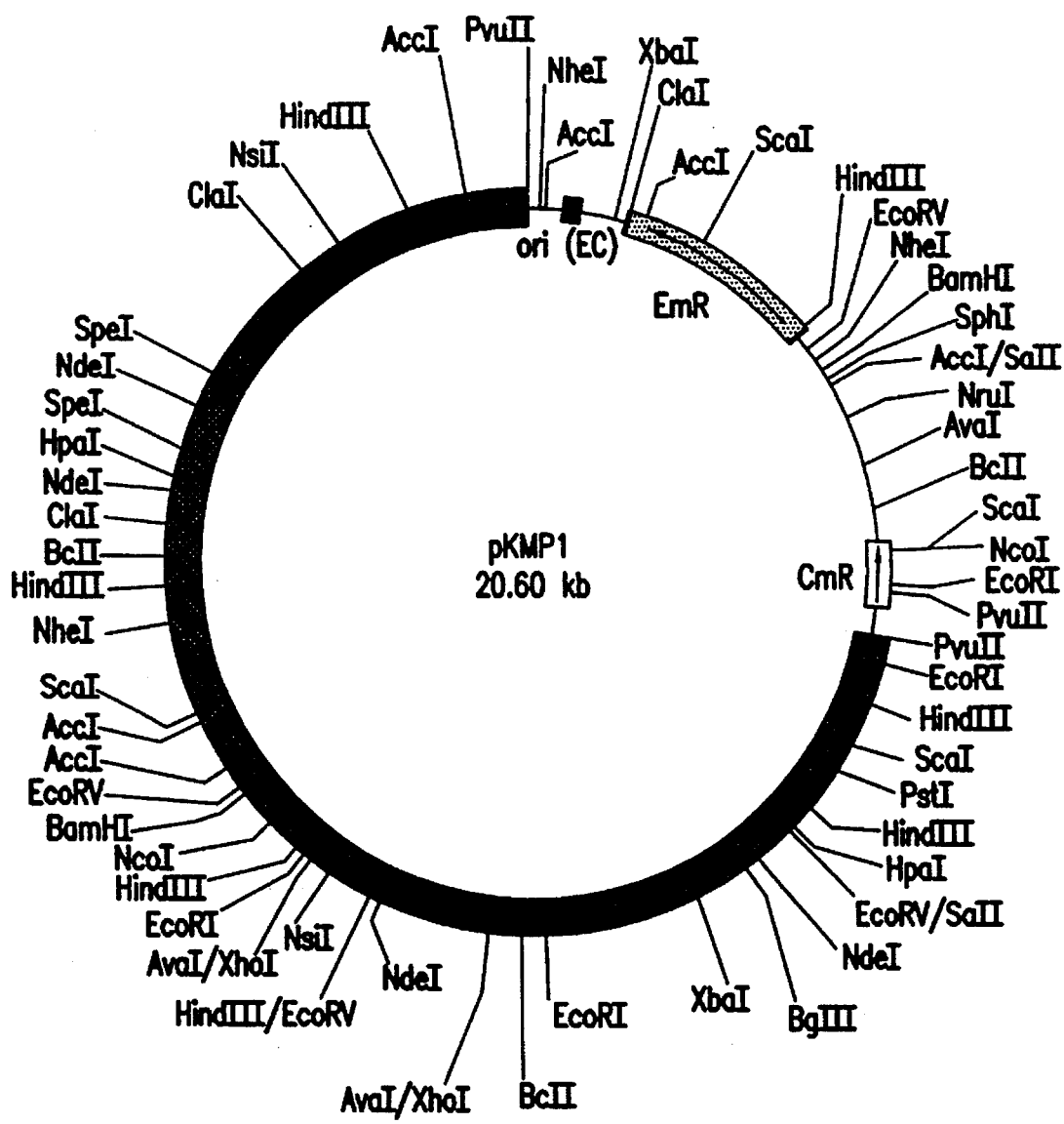
FIG. 1 represents a restriction endonuclease map of plasmid pKMP1. pKMP1 contains the 14.8 kbp PvuII fragment encoding the plasmid maintenance and replication sequences of pSK11L ligated to pVA891.

As used herein, the term "plasmid" refers to autonomously replicating extrachromosomal DNA which is not integrated into a microorganism's genome and is usually circular in nature. The term "gene" refers to a segment of DNA composed of a transcribed region and a regulatory sequence that makes transcription possible and can, either alone or in combination with other genes, provide the organism with an identifiable trait. "Open reading frames" are DNA sequences which contain genetic information capable of being transcribed to form a protein of a particular amino acid sequence. The term "trait" refers to detectable physical or functional characteristic of an organism. The term "phenotype" is a particular manifestation of a trait which corresponds to the presence of a particular gene. The term "homology" refers to two regions of DNA which contain regions of nearly identical DNA sequences. The term "host microorganism" refers to a microorganism which has been chosen to receive the genetic material including the integration vectors of the invention. The term "subclone", as used herein, includes the process of isolating a particular DNA sequence by restriction endonuclease digestion from one source of DNA and moving that DNA sequence into a vector which is used to transform a host organism so that the particular DNA sequence can be selectably amplified. "Transformant" refers to a microorganism which has been transformed with genetic material including the integration vectors of the invention.

Integration Vectors

The integration vectors of the invention are comprised of four DNA sequences operably joined together. The first DNA sequence encodes a microorganism plasmid replication and maintenance sequence. The plasmid replication and maintenance sequence provides for temperature sensitive loss of autonomously replicating or unintegrated plasmids including the integration vectors of the invention. The second DNA sequence encodes at least one selectable marker gene, preferably a food-grade marker gene. The third DNA sequence encodes a fragment of an insertion sequence which is substantially homologous to DNA sequences on the microorganism's genome. The fourth DNA sequence encodes at least one gene encoding a trait which is unstable.

The four DNA sequences are operably joined together. The four DNA sequences can be joined together to form a plasmid with little or no additional plasmid sequences. Alternatively, the four DNA sequences can be combined with additional plasmid DNA sequences. The four DNA sequences can be joined together in any order, and if combined with additional plasmid DNA sequences, the four DNA sequences can be separated from one another by other DNA sequences. The maximum size of DNA sequences which can be operably joined in an integration vector is that amount of DNA sequence which can be incorporated into a microorganism's genome and provide for stable inheritance of a gene encoding a trait. Preferably, the integration vector is comprised of less than about 100 kilobase pairs, and more preferably about 10–60 kilobase pairs, and most preferably about 20–50 kilobase pairs.

The DNA sequences can be joined together using standard recombinant DNA methods like those described by T. Maniatis et al. in *Molecular Cloning: A Laboratory Guide*, Cold Spring Harbor, N.Y. (1982) and S. Berger et al. in "Guide to Molecular Cloning Techniques", *Methods in Enzymology*, 152 (1987), which are hereby incorporated by reference.

In a preferred version, fragments of DNA sequences which have been identified to encode plasmid replication and maintenance functions, selectable marker genes, insertion sequences, and genes for traits which are unstable are isolated by restriction endonuclease digestion of plasmid or chromosomal DNA with particular restriction endonucleases. For example, a bacterial plasmid replication and maintenance sequence can be isolated from a plasmid like pSK11L by digestion with the restriction endonuclease PvuII. Each of the DNA fragments encoding a specific function can be individually sub-cloned into other plasmids and the plasmids can then be introduced into host microorganisms to yield transformed microorganisms.

The transformed microorganisms containing plasmids with the DNA sequences encoding the functions of interest are selected and grown to amplify the number of plasmids with the DNA sequence of interest. The DNA sequences of interest can be combined together by successively digesting plasmids with restriction endonucleases followed by ligation and selection for plasmids carrying a combination of the DNA sequences. For example, a plasmid carrying a PvuII fragment encoding a bacterial plasmid replication and maintenance sequence and a plasmid containing at least one selectable marker gene can be digested with the same or compatible restriction endonucleases, mixed together, and ligated. The resulting plasmids are then introduced into host microorganisms and host microorganisms containing a plasmid having both the plasmid replication and maintenance sequences and the selectable marker gene are selected and amplified.

Plasmids containing both DNA sequences described above and plasmids containing DNA sequence substantially corresponding to an insertion sequence are then digested with the same or compatible restriction endonucleases, mixed together and ligated. The resulting plasmids are introduced into host microorganisms and host microorganisms containing a plasmid having DNA sequences encoding plasmid replication and maintenance sequence, selectable marker gene, and an insertion sequence are selected and amplified.

The plasmid containing the three DNA sequences and a plasmid having DNA sequences encoding a gene which is unstable are digested with the same or compatible restriction endonucleases, mixed together, and ligated. The resulting plasmids are then introduced into host microorganisms and the host microorganisms containing plasmids with a DNA sequence encoding the plasmid replication and maintenance sequence, selectable marker gene, the insertion sequence, and the gene encoding a trait which is unstable are selected and amplified. The plasmids containing the four DNA sequences can be isolated from this population of host microorganisms and used as integration vectors.

In a preferred version, the integration vector containing the four DNA sequences is a food-grade integration vector and is further comprised of additional plasmid DNA sequences. A food-grade integration vector is a vector which contains DNA sequences which substantially correspond to DNA sequences present in the microorganisms used in food and/or dairy fermentations. The four DNA sequences and additional plasmid DNA sequences can preferably substantially correspond to DNA sequences present in the same genus of the microorganism. Alternatively, at least one of the four DNA sequences and/or the additional plasmid DNA sequences can substantially correspond to DNA sequences present in a different genus of microorganism used in food and/or dairy fermentations. Once a particular DNA sequence is identified as present in microorganisms which are used in food and/or dairy fermentations, substantially corresponding DNA sequences are those DNA sequences which are sufficiently related in sequence to provide the same function in the integration vector as that of the particular DNA sequence. By way of example, a gene encoding nisin resistance derived from *Lactococcus lactis* subsp. *lactis* can substantially correspond to a gene encoding nisin resistance derived from the bacteria *Streptococcus thermophilos*. Substantially corresponding DNA sequences can also be DNA sequences which preferably share about 60% to 100% DNA sequence homology, and more preferably about 75% to 100% DNA sequence homology to that particular DNA sequence. DNA sequences can be identified in microorganisms used in food and/or dairy fermentations by standard methods including selection of a microorganism with a specific phenotype, followed by amplification and identification of the DNA sequences associated with that trait.

The food-grade integration vector is capable of autonomous replication in a microorganism used in food and/or dairy fermentations. Preferably the integration vector does not require passage through another genus of bacteria not used in food and dairy fermentations to provide for either selection or amplification.

Additional plasmid DNA sequences are preferably derived from plasmids naturally present in microorganisms which are used in the food and/or dairy industry. Additional plasmid DNA sequences can be derived from plasmids in which the original DNA sequences corresponding to the plasmid replication and maintenance sequences have been deleted or are otherwise inoperative and the plasmid maintenance and replication sequence of the integration vector provides for replication and maintenance of the plasmid. Additional plasmid DNA sequences can include additional genes, like for example, other selectable marker genes or other genes which are unstable or other genes which provide the organism with enhanced functional capabilities. An example of a microorganism containing an integration vector and which exhibits enhanced functional capabilities is provided when additional plasmid DNA sequences are derived from a plasmid like pSK11L which encodes the lactose operon genes and DNA sequences corresponding to ISS1 insertion sequence. If the lactose operon genes are also present as one of the four DNA sequences of the integration vector, like for example as a selectable marker gene or as a gene encoding a trait which is unstable, the integration vector with the additional plasmid DNA sequence can provide the microorganisms with two copies of lactose operon which can increase the fermentative capabilities of the microorganism.

Suitable microorganisms which are used in food and dairy fermentations include bacteria of the Genus Pediococcus, Leuconostoc, Lactobacillus, Lactococcus, *Streptococcus thermophilos*, and Bacillus. Preferably, the microorganism is a bacteria of the Genus Lactococcus.

More preferably, the integration vector is comprised of DNA sequences substantially corresponding to DNA sequences present in bacteria of the Genus Lactococcus. For example, the first DNA sequence encoding a microorganism's plasmid replication maintenance sequence can substantially correspond to plasmid replication and maintenance sequences present in plasmids which can replicate in the Genus Lactococcus. The selectable marker gene is preferably a food-grade marker gene which substantially corresponds to selectable marker genes present in microorganisms of the Genus Lactococcus. The insertion sequences are preferably substantially homologous to insertion sequences present in the Genus Lactococcus.

1. Identification and Characterization of Microorqanism Plasmid Replication and Maintenance Sequences As used herein, a plasmid is an autonomously replicating extrachromosomal DNA, usually circular in nature. Plasmids can be a variety of sizes ranging from about 1.5 kb to greater than 100 kb. Plasmids present in host microorganisms can carry genes encoding traits which may or may not be present on the microorganisms chromosome. Plasmids can be present in a microorganism in a single copy or in multiple copies. Plasmids can be present as separate autonomously replicating units of DNA or can be integrated into a microorganism's chromosome. Integrated plasmids are joined to chromosomal DNA and are replicated along with the microorganism's chromosome. An autonomously replicating plasmid is also an unintegrated plasmid and has a plasmid replication and maintenance DNA sequence which provides for the replication and maintenance of the plasmid as the host microorganism replicates and divides. If the replication of the plasmid is not synchronized with the replication of the host microorganism's chromosomal DNA, plasmid DNA sequences can not be transmitted into progeny microorganisms and traits associated with the plasmid DNA are then be lost.

The integration vector of the invention is comprised of a first DNA sequence encoding a plasmid replication sequence and maintenance sequence. The plasmid replication and maintenance sequence provides for autonomous replication of the plasmid when introduced into a microorganism. The plasmid replication sequence can contain at least one open reading frame encoding a replication protein and a DNA sequence which acts as the initiation site for replication of the plasmid designated as the ori sequence. The plasmid maintenance sequence provides for inheritance of plasmid molecules by progeny microorganisms after the host microorganism replicates and divides.

The plasmid replication and maintenance sequence of the invention also provides for temperature sensitive loss of autonomously replicating or unintegrated plasmids including integration vectors. Autonomously replicating or unintegrated plasmids containing plasmid replication and maintenance sequences which exhibit the temperature sensitive phenotype are lost when the host microorganism is grown at a certain temperature range. While not meant to limit the invention in any way, it is believed that the plasmids containing plasmid replication and maintenance sequences which exhibit the temperature sensitive phenotype are not able to replicate as efficiently as normal plasmids at a certain temperature range so that as the host microorganism replicates and divides, the plasmid is not replicated and/or transmitted to the progeny microorganisms. The plasmids containing temperature sensitive replication and maintenance regions can be identified by identifying plasmid-containing host microorganisms which exhibit loss of a plasmid encoded trait or by detecting loss of plasmid DNA from microorganisms grown in a certain temperature range. Temperature sensitive loss can occur at any temperature range, but preferably occurs at higher temperature ranges and more preferably at temperature ranges greater than about 32° C.

Plasmid containing host microorganisms which lose a trait in a temperature sensitive manner can be examined for the loss of autonomously replicating or unintegrated plasmids including the integration vectors of the invention. Plasmid DNA can be isolated and the loss detected by standard recombinant DNA methods, like those provided in S. Berger et al. in *Guide to Molecular Cloning Techniques*, Academic Press, Inc. (1987) at pages 164–170, and D. Anderson et al., *Appl. Environmental Microbiol.*, 46:459 (1983), which are hereby incorporated by reference. An inability to isolate autonomously replicating plasmid DNA encoding a particular trait from a host microorganism grown at temperature ranges at which the host microorganism exhibits the temperature sensitive phenotype indicates the plasmid contains a temperature sensitive replication and maintenance sequence.

The temperature sensitive plasmid replication and maintenance sequence can be isolated from plasmids exhibiting temperature-sensitive loss by standard recombinant DNA methods. One way the sequence can be isolated is to isolate a plasmid exhibiting the temperature sensitive plasmid replication and maintenance phenotype and digest different samples of the plasmid separately with different restriction endonucleases. A different plasmid which does not replicate in the host microorganism at any temperature and carries at least one selectable marker gene can also be digested separately with the same or compatible restriction endonucleases. The plasmids digested with the same or compatible restriction endonucleases are mixed together and subcloned into a host microorganism. Host microorganisms which exhibit the phenotype associated with the selectable marker gene are selected and examined for the presence of plasmid DNA. Plasmids which can replicate in the host microorganism and which contain the selectable marker gene are examined for temperature sensitive plasmid replication and maintenance phenotype by growing the host microorganisms at a certain temperature range and examining the host microorganisms for loss of the trait with the selectable marker gene and/or loss of autonomously replicating plasmid DNA.

Alternatively, a temperature sensitive plasmid replication and maintenance sequence can also be generated by mutation of known plasmid origin and maintenance sequences. Plasmid replication and maintenance sequence can be identified as described above. Plasmids carrying the selected selectable marker gene and which carry the plasmid maintenance and replication sequences are subject to mutation by standard methodologies. The plasmids can be mutated by deleting portion of the plasmid, for example by removing certain portions with specific restriction endonucleases, by inserting DNA sequences like with Tn5 as described by F. DeBrujin et al., *Gene*, 27:131 (1984), which is hereby incorporated by reference, or by subjecting host bacteria carrying plasmids to mutagenic agents. Host bacteria and plasmids which exhibit temperature sensitive replication and maintenance are selected by identifying host microorganisms which lose the phenotype associated with the selectable marker when grown at a certain temperature range and/or by identifying host microorganisms which lose autonomously replicating plasmid DNA when grown at that temperature.

The plasmid maintenance and replication sequences are those capable of providing for temperature sensitive loss of autonomously replicating or unintegrated plasmid DNA, and preferably have DNA sequences which substantially correspond to DNA sequences present on plasmids in microorganisms which are used in food and/or dairy fermentation. Substantially corresponding DNA sequences are DNA sequences which are sufficiently related in sequence to provide for plasmid maintenance and replication. Substantially corresponding DNA sequences can also be DNA sequences which preferably share about 60% to 100% DNA sequence homology, and more preferably share about 75% to 100% DNA sequence homology to that particular plasmid maintenance and replication sequence.

Once identified, the temperature sensitive plasmid replication and maintenance sequences can be combined with the other four plasmid DNA sequences and/or additional plasmid DNA sequences to form an integration vector by standard recombinant DNA subcloning methods, as described previously. For example, the plasmid maintenance and replication sequence can be subcloned by isolating the plasmid maintenance and replication sequence on a particular restriction endonuclease fragment. The plasmid into which the plasmid replication and maintenance sequence is to be introduced and which carries at least one selectable marker gene is digested with the same or compatible restriction endonucleases. The plasmid replication and maintenance sequence fragments and the plasmid digest are mixed together and subcloned into a host bacteria. Host bacteria carrying the selectable marker gene and which exhibit temperature sensitive loss of autonomously replicating plasmid DNA can be selected.

In a preferred version, a plasmid which encodes the trait of lactose fermentation in bacteria from the Genus Lactococcus and which is lost upon the growth of the bacteria at temperature at least about 37° C., is isolated from the bacteria when grown at about 25° C. The plasmid is then separately digested with different restriction endonucleases like, for example, ClaI, XbaI and PvuII. A different plasmid like, for example, the E. coli plasmid pACYC184, which cannot replicate in the host bacteria and carries at least one selectable marker gene, is digested with the same or compatible restriction endonucleases. Plasmids digested with the same or compatible restriction endonucleases are mixed together and subcloned into a host bacteria of the Genus Lactococcus. Host bacteria exhibiting the trait of the selectable marker gene, like, for example, nisin resistance, are selected and examined for the presence of plasmid DNA. The plasmids from the transformants can also be examined to see if they exhibit the temperature sensitive loss of plasmid replication by growing the host bacteria at a temperature at least about 37° C. and examining the bacteria for loss of the trait associated with the selectable marker gene and/or loss of autonomously replicating plasmid DNA.

Suitable plasmids useful in the invention are plasmids present in bacteria of the Genus E. coli, Lactococcus, Lactobacillus, Leuconostoc, Pediococcus, Bacillus and Streptococcus thermophilos. The preferred plasmids are derived from bacteria of the Genus Lactococcus and exhibit temperature sensitive loss of autonomously replicating or unintegrated plasmids.

The invention also provides for a DNA sequence substantially corresponding to plasmid replication and maintenance sequences derived from the lactococcal plasmid pSK11L. Substantially corresponding DNA sequences are preferably those DNA sequences that share about 60% to 100% DNA sequence homology and preferably 75% to 100% DNA sequence homology with the plasmid maintenance and replication sequence of pSK11L. The plasmid replication and maintenance DNA sequence corresponds to the DNA sequence found on the 14.8 kilobase pair PvuII restriction endonuclease fragment of the pSK11L plasmid and is associated with increased temperature sensitive loss of pSK11L plasmids when Lactococcus lactis LM0230 is grown at temperatures of about 37° C. or greater.

A DNA sequence substantially corresponding to the plasmid replication sequence is provided on the 2.3 kilobase pair ScaI-SpeI fragment of the 14.8 kilobase pair PvuII fragment encoding the plasmid maintenance and replication sequence of pSK11L. A DNA sequence substantially corresponding to the second open reading frame and the upstream noncoding ori region containing direct and indirect repeats of the plasmid replication sequence on the 2.3 kb pair ScaI-SpeI fragment is that sequence designated SEQ ID NO:1. The predicted amino acid sequence associated with the second open reading frame is that sequence designated SEQ ID NO:2.

Mutants of the plasmid maintenance and replication sequence of the pSK11L plasmid or any other plasmid can be generated by standard methodologies as described previously. For example, deletion mutants can be generated by removing portions of the PvuII fragment with specific restriction endonucleases and ligating the plasmid back together. Insertion mutants are generated by utilizing the Tn5 system, as described previously. Plasmids with mutants of plasmid replication and maintenance sequence can be introduced into host bacteria and examined for temperature sensitive loss of autonomously replicating plasmid DNA.

2. Selectable Marker Genes

The integration vector of the invention is comprised of a second DNA sequence which encodes at least one selectable marker gene. Selectable marker genes encode traits which allow for selection and identification of microorganisms which contain the integration vector. The selectable marker gene can be present on the integration vector when it is present as an unintegrated or autonomously replicating plasmid or when it is integrated into a microorganism's genome. The selectable marker gene preferably provides a host microorganism with a new trait. The selectable marker gene can also be a gene encoding an unstable trait and/or provide the host microorganism with a new metabolic or other functional capability. Examples of suitable selectable marker genes include genes encoding antibiotic resistance, genes encoding carbohydrate metabolism, genes encoding bacteriophage immunity and resistance, and genes encoding bacteriophage lysin production, and mixtures thereof.

The selectable marker gene is preferably a food-grade selectable marker gene. Food-grade selectable marker genes are comprised of DNA sequences substantially corresponding to DNA sequences present in microorganisms which are used in food and/or dairy fermentations. Once identified as a selectable marker gene present in microorganisms used in food and/or dairy fermentations, DNA sequences which substantially correspond to a particular selectable marker gene sequence are preferably those DNA sequences which are sufficiently related to provide the same selectable marker trait. Substantially corresponding DNA sequences can also be DNA sequences which share about 60% to 100% DNA sequence homology and more preferably 75% to 100% DNA sequence homology to the DNA sequence of the particular selectable marker gene. The food-grade selectable marker gene preferably does not encode resistance to antibiotics used in human drug therapy. Suitable examples of food-grade selectable marker genes include nisin resistance genes, β-galactosidase genes, lactose metabolism genes, sucrose metabolism genes, bacteriophage resistance genes, bacteriocin resistance and immunity genes, and mixtures thereof.

The selectable marker gene is combined with the three other DNA sequences and/or additional plasmid DNA sequences to form an integration vector by standard recombinant DNA methods. For example, a fragment of DNA containing at least one selectable marker gene, like the lactose operon, can be obtained by restriction endonuclease digestion of chromosomal or plasmid DNA carrying the selectable marker gene. A plasmid carrying a temperature sensitive plasmid replication and maintenance sequence and a DNA sequence encoding a fragment of an insertion sequence is digested with the same or compatible restriction endonucleases. The fragment containing the selectable marker gene and the plasmid digest are mixed together and ligated. The resulting plasmids can be introduced into host microorganism and microorganism can be selected for the presence of the selectable marker gene and for temperature sensitive loss of autonomously replicating plasmid DNA. Plasmids containing the selectable marker gene, a temperature sensitive plasmid replication and maintenance sequence, and a DNA fragment encoding an insertion sequence can then be isolated from these host microorganisms.

Selection occurs when the host microorganisms is exposed to a selective condition and can grow in the presence of the selective condition. By way of an example, one selectable marker gene encodes erythromycin resistance. The selective condition employed to isolate host microorganism containing this selectable marker gene is to grow the microorganism in the presence of erythromycin. Only those host microorganisms carrying an erythromycin resistance gene can grow in the presence of erythromycin.

In a preferred version, a food-grade selectable marker gene encoding nisin resistance is identified in the bacteria of the Genus Lactococcus. Bacteria of the Genus Lactococcus, which are not nisin producers, are selected for resistance to nisin. A fragment of DNA encoding the gene for nisin resistance is isolated from nisin resistant bacteria by standard recombinant DNA methodologies. The nisin resistance gene is isolated as a DNA fragment by restriction endonuclease digestion and subcloned into a plasmid with at least one selectable marker gene. Resulting plasmids are introduced into host bacteria by electroporation and the transformed host bacteria are selected on the basis of at least one selectable marker gene like, for example, resistance to erythromycin. Transformant bacteria exhibiting the presence of the selectable marker gene are evaluated for nisin resistance by growth in the presence of nisin. Restriction endonuclease fragments conferring nisin resistance are identified.

The restriction endonuclease fragment encoding nisin resistance can be combined with a plasmid containing a temperature sensitive lactococcal plasmid replication and maintenance sequence and a DNA sequence encoding a fragment of an insertion sequence to form an integration vector as described previously. Resulting plasmids can be introduced into host bacteria of the Genus Lactococcus and host bacteria carrying the plasmids can be selected by selecting for the growth in the presence of nisin and for temperature sensitive loss of autonomously replicating or unintegrated plasmid DNA.

Accordingly, the invention also provides for a 1.454 kb DNA sequence substantially corresponding to the flanking regions and a gene encoding nisin resistance derived from *Lactococcus lactis* bv. *diacetylactis* DCR3 is designated as SEQ ID NO:3. A DNA sequence substantially corresponding to this gene encoding nisin resistance can provide for nisin resistance and can also preferably share about 60% to 100% DNA sequence homology, and more preferably about 75% to 100% DNA sequence homology to that of the nisin resistance gene. The DNA sequence is derived from the 7.8 kilobase pair EcoRI restriction endonuclease fragment of the pNP40 plasmid present in *L. lactis* subsp. *lactis* bv. *diacetylactis* DRC3. The DNA sequence substantially corresponds to the 1.454 kilobase pair EcoRI-KpnI restriction endonuclease fragment of the 7.8 kilobase pair EcoRI fragment of the pNP40 plasmid.

The 1.454 kb nucleotide sequence encoding the flanking regions and nisin resistance gene contains a single large open reading frame composed of 956 nucleotides. The open reading frame can encode a protein of 35,035 Daltons and 318 amino acids. The predicted amino acid sequence for the nisin resistance protein corresponds to that designated as SEQ ID NO:4.

Mutants of the nisin resistance gene and flanking sequences can be generated by standard methodologies. For example, mutants of the nisin resistant genes can be generated by digestion of the DNA fragment encoding the gene with additional restriction endonucleases. The restriction endonucleases can remove specific portions of the nisin resistance gene. The mutated DNA fragments encoding the mutated restriction endonuclease DNA fragments encoding nisin resistance can be subcloned into plasmids and then introduced into host bacteria. Host bacteria are then selected for nisin resistance.

3. Insertion Sequences

The integration vector of the invention is comprised of a third DNA sequence which encodes a fragment of an insertion sequence. The DNA sequence encoding the fragment of the insertion sequence is substantially homologous to DNA sequences present on the microorganism's genome and provide a site where integration of the integration vector into the microorganism's genome can occur. Substantially homologous DNA sequences are those DNA sequences which share sufficient DNA sequence homology to provide for sufficient homologous recombination between insertion sequences present on the integration vector and in the microorganism's genome. Sufficient DNA sequence homology is that amount which provides for homologous recombination at a frequency which allows for detection of microorganisms in which homologous recombination and integration of the integration vector has occurred. Substantially homologous DNA sequences preferably share regions with about 60% to 100% DNA sequence homology, and more preferably about 75% to 100% homology in the DNA sequence. The insertion sequence can be present in the integration vector or in the microorganism genome in a single copy or multiple copies.

The fragment of the insertion sequence corresponds to a portion of the insertion sequence which allows for homologous recombination with the sequences on the microorganisms genome and minimizes later excision and/or transposition of the integrated sequences. Specific examples of suitable insertion sequences include insertion sequence IS981, ISS1, IS1076, ISL1, IS904, and IS946. The DNA sequence encoding a fragment of the insertion sequence is preferably an insertion sequence which is substantially homologous to DNA sequences present on the chromosome in bacteria of the Genus Lactococcus, and more preferably fragments of the insertion sequence IS981.

A fragment of an insertion sequence is combined with the three other DNA sequences and/or additional plasmid DNA sequences to form the integration vector by standard recombinant DNA methods. For example, a DNA sequence encoding a fragment of the insertion sequence can be isolated from chromosomal or plasmid DNA by restriction endonuclease digestion. A plasmid carrying a temperature sensitive plasmid replication and maintenance sequence and at least one selectable marker gene can be digested with the same or compatible restriction endonucleases. The restriction endonuclease fragment with the insertion sequence is mixed with the plasmid digest and ligated. The resulting plasmids are introduced into host microorganisms, and the host microorganisms are selected for expression of the selectable marker trait and/or for temperature sensitive loss of autonomously replicating plasmid DNA. Plasmids from the selected host microorganisms are isolated and examined for the presence of insertion sequence by restriction endonuclease mapping and/or by hybridization of radio-labeled nucleotide probes specific for the insertion sequence by methods like those described in S. Berger, *Guide to Molecular Cloning Techniques*, Academic Press (1987).

In a preferred version, a fragment of a novel insertion sequence IS981 present in bacteria of the Genus Lactococcus is identified and cloned into the integration vector of the invention. The insertion sequence IS981 is identified as an insertion in the plasmid pMN14, the prolate phage sensitive derivative of plasmid pGBK17. The insertion sequence is present on a 3.2 kbp EcoRV restriction endonuclease fragment. The insertion sequence can be further digested with additional restriction endonucleases to generate fragments of the IS981 insertion sequence. Preferably, the insertion sequence fragment is digested with XbaI to generate a 0.7 kb restriction endonuclease fragment of the insertion sequence IS981. The 0.7 kb fragment of the insertion sequence is then subcloned into an XbaI site of a plasmid with a polylinker, like plasmid pSP73. The plasmid containing the insertion sequence and a plasmid containing a temperature sensitive plasmid replication and maintenance sequence and at least one selectable marker gene, like pKMP1-E, are digested with the same or compatible restriction endonucleases, mixed, ligated, and transformed into host bacteria. Host bacteria are screened for the expression of the selectable marker gene and plasmid DNA isolated from the selected bacteria is screened for the presence of the insertion sequence by restriction endonuclease mapping and/or by hybridization with radio-labeled nucleotide probes.

The invention also provides for a DNA sequence substantially corresponding to a DNA sequence encoding the insertion sequence IS981 designated as SEQ ID NO:5. A DNA sequence which substantially corresponds to the insertion sequence IS981 preferably shares 60–100% DNA sequence homology, and more preferably shares 75–100% DNA sequence homology. The insertion sequence IS981 is derived from a 3.2 kb EcoRV restriction endonuclease fragment of the plasmid pMN14.

Fragments of the insertion sequence can be generated by digestion with restriction endonucleases. A DNA sequence substantially corresponding to a 0.7 kbp XbaI restriction endonuclease fragment of the insertion sequence IS981 is also provided. Mutations of the insertion sequence IS981 can be obtained by standard methodologies, as described previously.

4. Genes Encoding an Unstable Trait

The integration vector of the invention is comprised of a fourth DNA sequence which encodes at least one gene encoding a trait which is unstable or other desirable genes to be integrated into the chromosome. An unstable trait is a trait with a phenotype that is lost upon replication and division of microorganism. The unstable trait encoded by a gene can be and is preferably present on a plasmid. Unstable traits are identified by examining the loss of the phenotype from a population of microorganisms as it is grown through a plurality of growth cycles. Unstable traits are those traits which are lost at a frequency exceeding the natural loss rate of traits present in the host microorganism. The natural loss rates of traits in the host microorganism can be defined by the natural mutation rate or loss frequency which is characteristic for a particular host microorganism. Natural mutation rates or loss frequency can be measured by determining the rate of loss of a phenotype associated with a trait encoded on the microorganism's chromosome and microorganisms which lose the phenotype are designated as spontaneous mutants. Natural mutation rates or loss frequencies of stable traits are preferably about $1 \times 10^{-5}$ to $1 \times 10^{-9}$, and more preferably about $1 \times 10^{-6}$ to $1 \times 10^{-9}$. Unstable traits preferably have a loss frequency at a rate of greater than about $1 \times 10^{-5}$ and more preferably at a rate of about $1 \times 10^{-2}$ to $1 \times 10^{-5}$.

Suitable examples of unstable traits include lactose metabolism genes, proteinase genes, citrate metabolism genes, bacteriocin production and immunity genes, nisin resistance genes, exopolymer genes, bacteriophage resistant genes, and mixtures thereof. Preferably, the unstable trait is one which provides the bacterial host with an industrial important phenotype including, for example, lactose fermentation.

The DNA sequence encoding a gene with an unstable trait is combined with the other DNA sequences to form the integration vector by standard recombinant DNA methods, as described previously.

In a preferred version, a 13 kbp (kilobase pair) restriction endonuclease fragment carrying the genes encoding the lactose operon is isolated by restriction endonuclease digestion of pSK11L plasmid obtained from *Lactococcus lactis* subsp. *cremoris* with Bcl1. The Bcl1 restriction endonuclease fragment encoding the lactose operon is subcloned into a plasmid with a polylinker. The plasmid with the fragment encoding the lactose operon is mixed with a plasmid containing a temperature sensitive plasmid maintenance and replication sequence, at least one selectable marker gene and a DNA sequence encoding a fragment of an insertion sequence, like for example pKMP10, digested with restriction endonucleases, ligated and transformed into host bacteria. Host bacteria can be selected by expression of the selectable marker gene and/or temperature sensitive plasmid and/or expression of the unstable trait and/or the presence of plasmid DNA with insertion sequences, and combinations thereof. Plasmids can be isolated from the selected bacteria which are useful as integration vectors.

5. Method for Increasing the Stability of Inheritance of Genes in a Microorqanism The invention also provides for a method of increasing the stability of inheritance of genes encoding traits in a microorganism by integration of the genes into a microorganism's genome. The method includes the steps of introducing an integration vector into a microorganism to yield a transformed microorganism, subjecting the transformed microorganism to a selective condition to yield a selected population of microorganisms and growing the selected population of microorganisms through a plurality of growth cycles to confirm that a population of microorganisms which exhibit an increase in the inheritance of a gene encoding a trait is obtained.

The integration vector is comprised of four DNA sequences operably joined together. The first DNA sequence encodes a microorganism's plasmid replication and maintenance sequence and provides for temperature sensitive loss of autonomously replicating or unintegrated plasmid DNA. The second DNA sequence encodes at least one selectable marker gene, preferably a food-grade selectable marker gene. The third DNA sequence encodes a fragment of an insertion sequence which is substantially homologous to DNA sequences on the microorganism's genome. The fourth DNA sequence encodes an unstable trait. The integration vector of the invention is preferably a food-grade integration vector, is comprised of DNA sequences substantially corresponding to DNA sequences present in the microorganisms used in food and/or diary fermentations, and further comprises additional plasmid DNA sequences.

The integration vector can be introduced into a microorganism by standard recombinant DNA methods including electroporation, protoplast transformation, transduction, or liposomal encapsulation. Microorganisms transformed are preferably microorganisms used in the production of food products, and more preferably a microorganism of a Genus selected from the group consisting of Lactococcus, Lactobacillus, Pediococcus, Leuconostoc, Bacillus, and *Streptococcus thermophilos*, and mixtures thereof.

The transformed microorganisms are subjected to a selective condition to select for microorganism which exhibit an increase in the stability of the inheritance of a gene encoding a trait. The selective conditions can include conducting a growth cycle of the transformed microorganisms at a temperature effective to inhibit temperature sensitive replication of the unintegrated or autonomously replicating integration vector, followed by conducting a growth cycle at an effective temperature to inhibit temperature sensitive unintegrated or autonomously replicating integration vector replication and in the presence of an effective amount of a selective agent to yield a selected population.

An effective temperature is that temperature range which provides for the loss of an unintegrated or autonomously replicating integration vector DNA from the transformed population of microorganisms. The effective temperature can vary but is preferably a temperature range of about 32° C. to 40° C., and more preferably about 37° C. to 40° C.

Suitable selective agents are chosen dependant upon the type of selectable marker gene present in the integration vector. By way of example, if the selectable marker gene is erythromycin resistance, the selective agent employed in the method is erythromycin. An effective amount of the selective agent is that amount which allows for detectable growth of the transformed microorganism carrying the selectable marker gene and inhibition of the growth of those microorganisms which do not carry the selectable marker gene.

A selective condition can also further include selecting transformed microorganisms which exhibit the selectable marker gene and lack unintegrated or autonomously replicating integration vector DNA sequences when grown at temperatures at which unintegrated or autonomously replicating integration vector DNA sequences are lost. The effective temperature at which autonomously replicating integration vector DNA is lost depends on the temperature sensitive plasmid replication and maintenance sequence phenotype. The preferred temperature ranges are about 32° C. to 40° C., and more preferably about 38° C. to 40° C. Microorganisms lacking unintegrated or autonomously replicating integration vector DNA can be detected using standard recombinant DNA methods.

The selected population of microorganisms is grown through a plurality of growth cycles to confirm that a population of microorganisms which exhibit an increase in the stability of inheritance of a gene encoding a trait is obtained. A plurality of growth cycles is preferably at least about 50 generations, and more preferably about 50–100 generations of growth. An increase in the stability of the inheritance of the gene encoding the trait can be determined by comparing the percentage of microorganisms loss frequency associated with the loss of the phenotype associated with a trait when it is present on unintegrated or autonomously replicating integration vectors with the loss frequency associated with the loss of the same phenotype associated with the trait when it is present in an integrated vector in the microorganism's genome after a plurality of growth cycles. An increase in the stability of inheritance of a gene encoding a trait is preferably a decrease in the loss frequency of the phenotype of the trait at least about 10-fold, and more preferably about 10- to 90-fold when compared to the loss frequency of the phenotype associated with a trait when encoded on an autonomously replicating plasmid.

Although it is not meant to limit the invention in any way, it is believed that the method of the invention results in integration of the integration vector into the microorganism's genome by homologous recombination preferably between insertion sequences present on the integration vector and substantially homologous insertion sequences on the microorganism's genome. Homologous recombination may occur between other sequences present on the integration vector and on the microorganism's genome. Homologous recombination is catalyzed by recombination enzymes which direct the matching, cutting, and ligating of the DNA sequences so that homologous recombination can occur between vector insertion sequences and DNA sequences on microorganisms genome in microorganisms having the recombination enzymes. It is believed that the stability of the marker traits and the unstable traits is achieved by integration of the vector encoding these traits into the microorganism's genome.

In a preferred version, an integration vector having a temperature sensitive plasmid replication and maintenance sequence substantially corresponding to the lactococcal plasmid replication and maintenance sequence of pSK11L, a food-grade selectable marker gene, a fragment of the lactococcal insertion sequence IS981, and genes encoding the lactose operon are introduced into a bacteria of the Genus Lactococcus by electroporation. Transformed bacteria are selected by growth in the presence of a selective agent or by the presence of lactose fermentation. Microorganisms exhibiting more stable inheritance of the selectable marker genes or lactose fermentation are selected by growth at a temperature effective to inhibit autonomously replicating unintegrated plasmid DNA and in the presence of the selective agent, like nisin. To confirm stability, the selected microorganisms are grown for a plurality of growth cycles, preferably about 50–100 generations. Bacteria which show an increase in the stability of the inheritance of a gene encoding a trait after the plurality of growth cycles can be obtained.

6. Microorganisms Which Exhibit an Increase in the Stability of the Inheritance of the Gene Encoding a Trait The invention also provides for microorganisms with at least one integration vector integrated into the genome and which exhibit an increase in the stability of the inheritance of the gene encoding a trait. The microorganisms are preferably microorganisms used in the production of food products. The trait which is stabilized is preferably a trait of industrial value.

Suitable microorganisms include bacteria from the Genus Lactococcus, Lactobacillus, Pediococcus, Leuconostoc, Bacillus, and *Streptococcus thermophilos*, and mixtures thereof. Preferably, the microorganism is a bacteria of the Genus Lactococcus.

Suitable traits can be plasmid encoded and can exhibit unstable inheritance. Although not meant to limit the invention in any way, it is believed that the plasmid encoded traits can be easily lost as the host microorganism replicates and divides, causing the loss of the traits associated with the genes encoded by the plasmid. Genes encoding suitable traits include lactose metabolism genes, proteinase genes, citrate metabolism genes, bacteriocin production and immunity genes, nisin resistance genes, exopolymer genes, bacteriophage resistance genes, and mixtures thereof.

The integration vector is comprised of four DNA sequences operably joined together. The first DNA sequence encodes a microorganism's plasmid replication and maintenance sequence which provides for temperature sensitive loss of autonomously replicating or unintegrated plasmid DNA. The second DNA sequence encodes at least one selectable marker gene, preferably a food-grade selectable marker gene. The third DNA sequence encodes a fragment of an insertion sequence which is substantially homologous to DNA sequences on the microorganism's genome. The fourth DNA sequence encodes an unstable trait. The integration vector of the invention is preferably a food-grade integration vector and is comprised of DNA sequences substantially corresponding to DNA sequences present in microorganisms used in food and/or dairy fermentations and further comprises additional plasmid DNA sequences.

The integration vector is preferably integrated into a microorganism's genome. The integration vector can be integrated in single copy or multiple copies, and at a single site or multiple sites on the microorganism's genome. The integration vector preferably integrates at the site of an insertion sequence homologous to insertion sequences present in the integration vector, but can also integrate into a microorganism's genome at other sites with homologous DNA sequences. A portion of the integration vector carrying an unstable trait can be integrated, but preferably substantially all of the integration vector is integrated into the microorganism's genome. The maximum amount of integration vector DNA sequence which can be integrated into a microorganism's genome at a single site is that amount of a DNA which can be integrated and provide for an increase in stability in the inheritance of a gene encoding a trait. The size of the integration vector integrated at one site in a microorganism's genome is preferably less than about 100 kilobases, and more preferably about 5–60 kilobases, and most preferably about 5–20 kilobases.

An increase in the stability of the inheritance of a gene encoding a trait is detected by growing the transformed microorganisms through a plurality of growth cycles and comparing the loss frequency of a phenotype associated with a trait, like for example, the selectable marker gene, when it is present in the microorganism on an unintegrated or autonomously replicating vector with the reversion frequency of the phenotype associated with the same trait when it is present on an integrated vector in the microorganism's genome. A plurality of growth cycles is preferably at least about 50 generations, and more preferably about 50–100 generations. An increase in the stability of the inheritance of a trait is preferably a decrease in the loss frequency of at least about 10-fold, and more preferably about 10- to 90-fold.

Although not meant to limit the invention in any way, it is believed that the increase in stability of the inheritance of a gene encoding a trait is, in part, due to the integration of plasmid encoded genes into the microorganism's genome. The integration of the plasmid encoded genes into the microorganism's genome makes it less likely that these traits will be lost as the host microorganism replicates and divides, as the integrated genes will be replicated as a part of the microorganism's genome. Stability of inheritance of the integrated genes can also be enhanced by using a fragment of an insertion sequence in the integration vector which is sufficient to provide for homologous recombination with the microorganism's genome and minimize subsequent excision and/or transposition events.

In a preferred version, an integration vector containing temperature sensitive plasmid replication and maintenance sequences derived from the lactococcal plasmid pSK11L, at least one selectable marker gene like nisin resistance, a fragment of the lactococcal insertion sequence IS981, and genes encoding the lactose operon is introduced into bacteria of the Genus Lactococcus. Bacteria with the integration vector integrated into their bacterial genome, which express the selectable marker gene, and which show an increase in the stability of the inheritance of the lactose operon genes are selected and amplified.

The invention also provides for a microorganism, *Lactococcus lactis* subsp. *lactis* MG1363 containing the integration vector pKMP10. The pKMP10 integration vector contains the replication and temperature sensitive maintenance regions from pSK11L, the erythromycin resistance selectable marker gene, and the internal 0.7 kb XbaI fragment of insertion sequence IS981. The transformed microorganism is designated MG1363 (pKMP10) and has been deposited with the American Type Culture Collection, Rockville, Md., in accordance with the Budapest Treaty on Feb. 25, 1992. The microorganism has been assigned ATCC No. 68917.

The invention will be described with reference to various specific and preferred embodiments and techniques, however, it should be understood that many variations and modifications can be made while remaining within the spirit and scope of the invention.

EXAMPLE I

Identification and Characterization of Bacterial Plasmid Replication and Maintenance Sequences 1. Bacterial Strains and Plasmids The *L. lactis* strains used in this study included LM0230, a plasmid-free, prophage-free derivative of C2, and JF3216, an LM0230 transformant containing pSK11L, a lactose plasmid from *L. cremoris* SK11. The *L. cremoris* strain used was EB$_5$, a plasmid-free derivative of KR1. Strains LM0230 and EB$_5$ were grown at 32° C. in M17 broth supplemented with 0.5% glucose (M17-G). Transformants derived from these strains were grown at 25° C. in M17-G containing erythromycin (Em) (10 μg/ml). Strain JF3216 was grown at 25° C. in M17 broth supplemented with 0.5% lactose. The *Escherichia coli* plasmid used to clone the replication region of pSK11L was pVA891, a derivative of pACYC184 containing the pAMβ1 Em$^r$-encoding gene (Erythromycin resistance). pVA891 and its derivatives were maintained in *E. coli* XL1-Blue (Stratagene, La Jolla, Calif.) grown at 37° C. with shaking in LB broth supplemented with chloramphenicol (25 μg/ml) or Em (30 μg/ml).

2. Method of Isolation of and Restriction Analysis of Plasmid DNA

*L. lactis* plasmid DNA was isolated by the method of Anderson and McKay (D. Anderson et al., *Appl. Environ. Microbiol.*, 46:549 (1983)). *E. coli* plasmid DNA was isolated by either an alkaline lysis procedure (T. Maniatis, *Molecular Cloning: A Laboratory Manual*, Cold Spring Harbor Laboratory (1982)) or the rapid small-scale lysis procedure of Rodriquez and Tait, in *Recombinant DNA Techniques: An Introduction*, Addisson Wesley Publishing Co., Reading, Mass. (1983). Large-scale plasmid isolations were followed by DNA purification through a CsCl-ethidium bromide density gradient. Restriction enzymes were purchased from Life Technologies, Inc. (Grand Island, N.Y.) or Boehringer Mannheim Biochemicals, Inc. (Indianapolis, Ind.), and digestions were performed as recommended by the manufacturers. Agarose gel electrophoresis was performed by using Tris-acetate-EDTA buffer (pH 8.0) at 4.0 V/cm, followed by staining in ethidium bromide (0.5 µg/ml). DNA ligations were performed with T4 DNA ligase (Life Technologies, Inc.), and the ligated DNA was introduced by electroporation with a Gene Pulser (Bio-Rad Laboratories, Richmond, Calif.) into either *E. coli*, as recommended by the manufacturer, or into LM0230 or $EB_5$, as described by Feirtag in *Appl. Environ. Microbiol.*, 57, 539 (1991). When necessary, deletion derivatives of pKMP1 were constructed in *E. coli* and then electroporated into LM0230 and $EB_5$.

3. Physical and Genetic Map of pSK11L

To determine the physical relationship between the replication, stability and temperature-sensitive maintenance regions of pSK11L and other pSK11L genetic loci, a restriction map of pSK11L was prepared and the positions of known genetic loci were determined. pSK11L was 47.3 kbp long. The replication region and regions affecting stability were localized on the basis of the studies described below for the 14.8-kbp PvuII fragment of pSK11L cloned in pKMP1. The lactose operon was determined to be within the 13-kbp BclI fragment by subcloning. One end of the operon was found to extend beyond the BglII site because of the inability to recover $Lac^+$ transformants when the smallest BglII fragment was deleted from pSK11L. The other end of the operon included the 4.3-kbp XhoI fragment, since this fragment encodes the phospho-β-galactosidase gene of the operon. The large size of the pSK11L lactose operon is in accordance with previously characterized lactococcal lactose operons which have been shown to contain not only the three genes of the lactose phosphoenolpyruvate phosphotransferase system but also the tagatose-6-phosphate pathway genes and an open reading frame (ORF) with an undetermined function.

Southern transfers were performed as described by K. Polzin et al., *J. Bacteriol.*, 16:5481 (1987), by using Nytran membranes (Schleicher & Schuell, Inc., Keene, N. H.) prepared as suggested by the manufacturer. Probe labeling, hybridization, and detection were conducted by using the Genius kit (Boehringer Mannheim Biochemicals) as recommended by the manufacturer. DNA fragments used as probes were isolated by using DEAE-cellulose (Schleicher & Schuell).

pSK11L contained two lactococcal insertion elements. Southern hybridization using the internal 0.7-kbp DraI fragment of ISS1 revealed regions with homology to ISS1 located on opposite sides of the lactose operon. Southern hybridization with the internal 0.7-kbp XbaI fragment of IS981 revealed that pSK11L also contained a copy of this insertion element immediately upstream of or slightly overlapping the lactose operon.

4. Cloning of the pSK11L Replication Origin pVA891 is a derivative of *E. coli* plasmid pACYC184 containing the pAMβ1 $Em^r$ gene which is expressed in lactococci. Several attempts to transform pVA891 into *L. lactis* LM0230 verified that this plasmid does not replicate in this host, as no $Em^r$ transformants were recovered. To clone the replication origin, pSK11L was digested separately with ClaI, XbaI, and PvuII and shotgun cloned into pVA891 and $Em^r$ LM0230 transformants were selected. No transformants were recovered by using ClaI fragments, despite two transformation attempts. Two transformants were recovered from the XbaI cloning experiment, but these contained no detectable plasmid DNA and were not examined further. However, one clone, which contained the 14.8-kbp PvuII fragment of pSK11L ligated to pVA891, was recovered from the PvuII cloning experiment. This plasmid was named pKMP1 (FIG. 1) and presumably carried the replication region of pSK11L.

5. Localization of the Replication Region and DNA Sequence of the pSK11L Replicon A number of deletion derivatives of pKMP1 were constructed in *E. coli* and screened for the ability to replicate in *L. lactis* LM0230. Successful transformation of LM0230 with a deletion derivative indicated that the deletion did not inactivate the lactococcal replication region. Failure to recover $Em^r$ transformants implied that the lactococcal replication region had been disrupted. Deletion of the region to the left of the ScaI site (pKMP1-SP) and deletion of the small 0.7-kbp SpeI fragment (pKMP1-Se) did not prevent replication. However, deletion of the region to the left of the NheI site (pKMP1-Nh) and deletion of the small 0.8-kbp NdeI fragment (pKMP1-Nd) abolished replication in LM0230. Therefore, the replication region was localized to the 2.3-kbp ScaI-SpeI fragment of pKMP1. This was confirmed by subcloning this fragment into pVA891 and transforming LM0230 to $EM^r$ with the resulting plasmid (pKMP1-SS).

Tn5 mutagenesis was then used to confirm the location and further localize the pKMP1 replication region. One hundred and two Tn5 insertions into pKMP1 were mapped, of which 58 occurred in the 14.8-kbp PvuII fragment. Forty-two insertions were in the 6.9-kbp XbaI-ClaI fragment, and two were in the adjacent 2.6-kbp ClaI fragment overlapping the replication region. A 2.4-kbp region overlapping the replication region was devoid of Tn5 insertions.

Twenty-eight pKMP1::Tn5 derivatives were screened for the ability to replicate in LM0230 by attempting to recover $Em^r$ LM0230 transformants containing these plasmids. The presence of pKMP1::Tn5 in $Em^r$ transformants was verified by restriction digestion analyses. Only Tn5 insertions in the 2.3-kbp ScaI-SpeI fragment abolished pKMP1 replication ability. However, the insertion just to the right of the ScaI site did not affect replication, indicating that the replication region did not span the entire 2.3-kbp region but began slightly to the right of the ScaI site. These results verified that the pKMP1 replication region was in the 2.3-kbp ScaI-SpeI fragment. Transformation of LM0230 with certain pKMP1::Tn5 derivative with insertions in the replication region did produce $Em^r$ transformants; however, the frequency was significantly lower than pKMP1 with Tn5 insertions in other regions and these transformants contained either no detectable plasmid DNA or a deleted and/or rearranged form of pKMP1.

The entire 2.3-kbp ScaI-SpeI fragment was sequenced in both directions and found to contain two complete ORFs (ORF1 and ORF2) and one incomplete ORF (ORF3) as reported by J. Horng et al. *J. Bact.*, 173:7573 (1991), which is hereby incorporated by reference. ORF1 was short (381 bp), and its 5' region did not contain sequences resembling the lactococcal ribosome-binding site (RBS) and promoter sequences. ORF1 did not appear to be necessary for pSK11L replication, since Tn5 insertions within this region did not inactivate pKMP1 replication. ORF3 was preceded by the lactococcal RBS and promoter sequences; however, its coding sequence was truncated at the SpeI site. Truncation or deletion of ORF3 did not inactivate replication but did affect plasmid stability in both *L. lactis* LM0230 and *L. cremoris* $EB_5$, as demonstrated below.

The DNA sequence of ORF2 and the upstream noncoding ori sequence substantially correspond to that of SEQ ID NO:1 and the corresponding predicted amino acid sequence of ORF2 corresponds to that of SEQ ID NO:2. ORF2 is 1,155 bp long and has the capacity to encode a polypeptide (designated Rep) of 385 amino acids with a molecular weight of 45,639. The putative Rep protein is necessary for pSK11L replication, as Tn5 insertions within its coding region abolished the pKMP1 replication ability in *L. lactis* LM0230. ORF2 was preceded by the canonical RBS and −10 and −35 promoter sequences of lactococci.

The sequence upstream of the pSK11L rep gene encoded by ORF2 (designated ori; nucleotides 1 to 288) did not encode a polypeptide but contained several salient structural features typical of a replication origin. These included an 11-bp imperfect direct repeat (Ia and Ib; nucleotides 15 to 149) separated by 3 bp and another 22-bp sequence tandomly repeated three and one-half times (IIa to IId; nucleotides 205 to 283). All of the 22-bp repeats were perfect, except for the second set, which contained a single mismatch at position 1 (T replaced by C). Similar repeated structures have been implicated in mediation of plasmid incompatibility and regulation of plasmid copy number. pSK11L contained a stable stem-loop structure (nucleotides 90 to 138; G=−11.8 kcal [1 cal= 4.184 J]/mol) which included the first set (Ia) of the 11-bp direct repeat.

6. Identification of Regions contributing to Plasmid Stability and Temperature Sensitive Maintenance Maintenance of pSK11L has been shown to be temperature sensitive in *L. lactis* LM0230. To determine whether pKMP1 encodes the temperature-sensitive maintenance phenotype and the plasmid replication function of pSK11L, the time course elimination of pKMP1 was measured at 25 and 37° C. In the absence of Em, the proportion of Em$^r$ cells decreased at about the same rate at both temperatures, resulting in 82% and 83% Em$^r$ cells after three generations at 25° and 37° C., respectively. However, after three generations, the percentage of Em$^r$ cells decreased faster in the 37° C. culture than in the 25° C. culture, resulting in 38% and 72% Em$^r$ cells, respectively, after 8.3 generations.

Regions affecting plasmid stability in LM0230 were identified by comparing the loss rates of pKMP1 and its deletion derivatives from *L. lactis* LM0230 during growth at 25° C. These results implicated several regions as potentially being involved in stabilization or destabilization of pKMP1 in LM0230. Deletion to the first BclI site (pKMP1-Bc) had no significant effect on plasmid stability (see FIG. 2). However, deletion of three regions, 1 (pKMP1-A), 3 (pKMP1-Se), and 5 (compare loss of pKMP1-SPH with that of pKMP1-SP), resulted in a two- to threefold increase in plasmid loss, suggesting that these regions stabilize pKMP1 in LM0230 (see FIG. 2). A region which potentially destabilizes pKMP1 in LM0230 was also identified. Deletion of region 2a (pKMP1-E) resulted in a plasmid significantly more stable than pKMP1.

Figure 2:
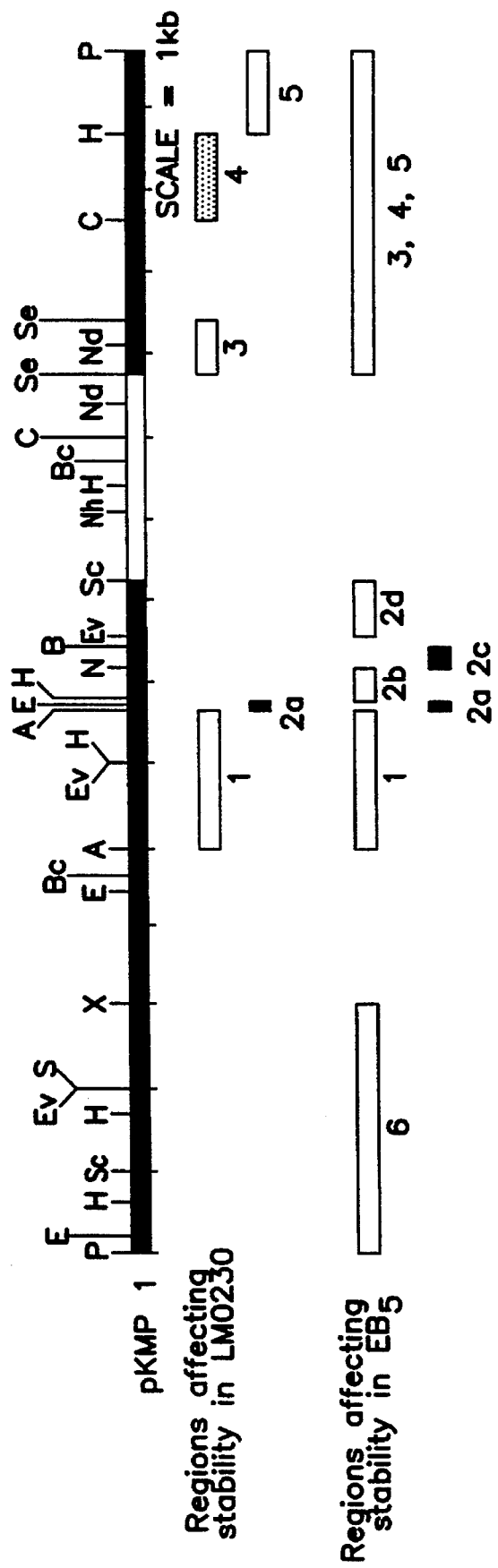
FIG. 2 represents a restriction endonuclease map of the 14.8 kbp PvuII fragment derived from pKMP1 which encodes the plasmid maintenance and replication sequence of pSP11L. Deletion mutants of this DNA sequence are also identified. The open block on the map indicates the pSK11L replication region. Open bars below the map indicate regions whose deletion decreased stability. Solid bars indicate regions whose deletion increased stability. The speckled bar indicates the region whose deletion abolished the temperature sensitive maintenance phenotype.

Regions of pKMP1 involved in temperature-sensitive maintenance were determined by comparing the loss frequencies of pKMP1 and its deletion derivatives at 25, 32, 37, and 39° C. (FIG. 2). No significant difference between loss frequencies at 25° and 32° C. was observed. However, plasmid loss rates increased an average of 6-fold at 37° C. and at least 10-fold at 39° C. compared with loss frequencies at 25° C. for all plasmids except pKMP1-C and pKMP1-SS. Therefore, the temperature required for expression of the temperature-sensitive maintenance phenotype in *L. lactis* LM0230 appeared to lie between 32° and 37° C. pKMP1-C, although slightly less stable than pKMP1 at 25° C., showed no significant increase in loss frequency at 39° C. pKMP1-C differed from pKMP1 and other deletion derivatives in that it lacked region 4 (1.2-kbp ClaI-HindIII fragment). These results suggested that region 4 is responsible for temperature-sensitive maintenance of pKMP1 in *L. lactis* LM0230.

Examination of the loss rates of pKMP1 and its deletion derivatives from *L. cremoris* EM$_5$ during growth at 25° C. revealed that except for plasmids lacking region 2b (pKMP1-N) or 2d (pKMP1-SP), pKMP1 and all of the pKMP1 derivatives tested were more stable in *L. cremoris* EB$_5$ than in *L. Lactis* LM0230. Deletion of several regions had different effects in EB$_5$ than in LM0230. Deletion of regions 2b (pKMP1-N), 2d (pKMP1-SP), and 6 (pKMPi-X), which had no effect on stability in LM0230, caused greater than 10-fold increased in plasmid loss in EB$_5$ (FIG. 2). Deletion of region 2c (pKMP1-B) caused decreased plasmid loss in EB$_5$, while deletion of this region had no effect in LM0230. However, regions which behaved similarly in EB$_5$ and LM0230 were also identified. Deletion of regions 1(pKMP1-A) and 3 (pKMP1-BS) destabilized pKMP1 in both LM0230 and EB$_5$, while deletion of region 2a (pKMP1-E) stabilized the plasmid in both strains. Deletion of region 6 and regions 3, 4, and 5 together resulted in a plasmid (pKMP1-SBH) as unstable as the minimum replicon (pKMP1-SS), despite the presence of stabilizing region 1. pKMP1-SPH and pKMP1-C, which individually lack LM0230 stabilization region 5 and temperature-sensitive maintenance region 4, respectively, were not tested in EB$_5$.

Temperature-sensitive maintenance of pKMP1 and its deletion derivatives in EB5 was determined by comparing the loss frequencies at 25°, 32°, and 37° C. (EB$_5$ does not grow at 39° C.). No obvious difference between plasmid loss rates was observed for growth at 25° and 32° C. However, all plasmids except pKMP1-N, which lacks region 2b, showed an increase (average, 2.6-fold) in loss frequency at 37° C. compared with that at 25° C. Therefore, pKMP1 and its derivatives appeared to produce a temperature-sensitive maintenance phenotype in both LM0230 and EB$_5$.

EXAMPLE II

Identification and Molecular Characterization of a Food Grade Selectable Marker Gene Encoding Nisin Resistance 1. Bacterial Strains and Plasmids

*L. lactis* strains are propagated at 32° C. in M__ broth (42) supplemented with 0.5% glucose. *L. lactis* strains carrying the erythromycin resistance (Em$^r$) marker of small pSA3 or pPGB301 were grown in the presence of erythromycin at 3 μg/ml. *L. lactis* strains containing the nisin resistance marker of pNP40 were grown in M17-6 broth containing nisin at 40 IU/ml. The MIC of nisin for *L. lactis* strains was determined as described previously. pFM011 was subcloned into the vector pUC118, pBluescript SK(+) (Stratagene, La Jolla, Calif.), or pSA3 with transformation into *Escherichia coli* XL-1 Blue (Stratatene). The *E. coli* strains were propagated 37° C. with agitation in LB broth supplemented with 50 μg/ml for the pUC118 or pBluescript SK(+) derivatives or 100 μg of chloramphenicol per ml for pSA3 derivatives.

Plasmid preparation agarose gel electrophoresis and cloning were conducted as described in Example I.

2. Localization Subcloning and DNA Sequence of the Nisin Resistance Gene

Figure 3:
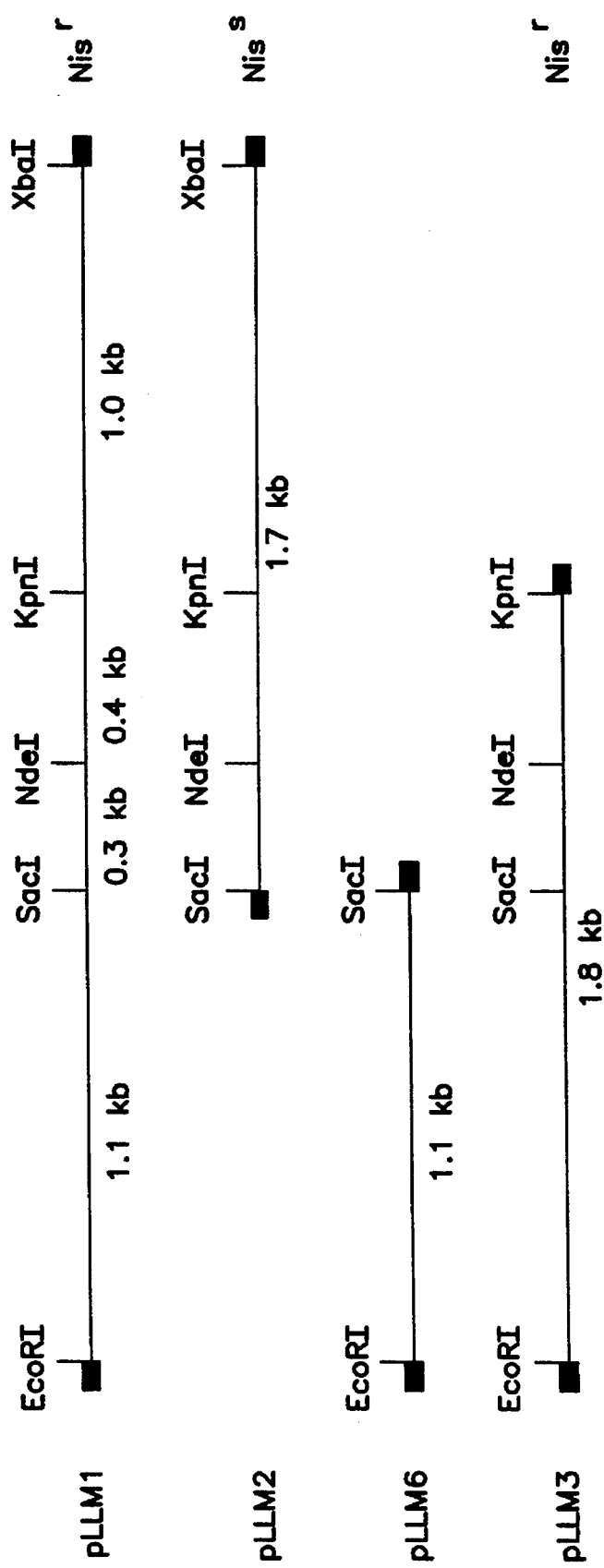
FIG. 3 represents the physical restriction map and subcloning of the EcoR1-XbaI fragment encoding the gene associated with nisin resistance. The entire 2.8 kb fragment and the two overlapping fragments, EcoR1-KpnI and SacI-XbaI, were cloned with pSA3 and introduced into L. Lactis subsp. lactis LM0230. The nisin resistance phenotype of the resulting transformants is indicated on the right. Nis$^r$ represents nisin resistance with an MIC of 160 IU/ml; Nis$^s$ represents nisin sensitivity with an MIC of 20 IU/ml.

The nisin resistance (Nis$^r$) phenotype was previously localized on a 2.6-kb EcoRI-XbaI fragment. Subsequent analysis of this fragment has determined it to be 2.8 kb long. Single restriction sites were mapped on this EcoRI-XbaI fragment for the endonucleases SacI, NdeI, and KpnI (FIG. 3). By using the four enzymes XbaI, EcoRI, KpnI, and SacI, all six possible fragments were cloned into *E. coli* X1-1 Blue with pUC118 or pBluescript SK(+) to generate pLLM1 through pLLM6. To further localize the nisin resistance determinant, the overlapping 1.8-kb EcoRI-KpnI and 1.7-kb SacI-XbaI fragments (FIG. 5) were excised from the pUC118 polycloning site with EcoRI and XbaI and ligated into the shuttle vector pSA3, which was also digested with EcoRI and XbaI. The two recombinant plasmids pLLM7 and pLLM8, formed with the EcoRI-KpnI and SacI-XbaI fragments, respectively, were transformed into plasmid-free *L. lactis* subsp. *lactis* LM0230; transformants were selected with the erythromycin resistance marker of pSA3. The nisin resistance of the transformants was evaluated, as shown previously, the 2.8-kb EcoR1-XbuI fragment confers a level of nisin resistance equivalent to that encoded by the entire 7.8 kb EcoR1 fragment of pNP40, which, when inserted into LM0230, resulted in an MIC of 160 IU of nisin per ml. This level of resistance is about half that conferred by intact pNP40 in the LM0230 background. The MIC of nisin for plasmid-free LM0230 was 20 IU per ml. The 7.8 kb EcoR1-KpnI subfragment conferred a level of nisin resistance equivalent to that conferred by the entire 2.8 kb fragment (a nisin MIC of 160 IU/ml). The transformant containing the 1.7 kb SaciI-XbuI fragment was nisin sensitive (FIG. 3). Therefore, the nisin resistance determinant appeared to be encoded entirely by the 1.8 kb EcoR1-KpnI fragment.

Cloning of random NdeI fragments from pBF61 into the NdeI site of pFG010 did not disrupt the Nis' phenotype. Therefore, the gene encoding nisin resistance does not overlap the NdeI site of the EcoR1-KpnI fragment (FIG. 3). Since subcloning indicated that the ScaI-XbuI fragment did not encode nisin resistance, the resistance determinant appeared to be located between the EcoR1 and NdeI restriction sites (FIG. 3).

DNA fragments were subcloned into pUC118 or pBluescript SK(+), and denatured double-stranded plasmid DNA (e.g. 3 µg) was sequenced bidirectionally by the dideoxy-chain termination method. A Sequenase version 2.0 DNA sequencing kit (United States Biochemical, Cleveland, Ohio) was used as recommended by the manufacture, and the synthesized DNA was labeled with $S^{35}$-dATP (New England Nuclear, Boston, Mass.). The plasmid DNA was denatured and the primers were annealed and a primer-to-template molar ratio of 4:1 were used in the denaturation mix. Electrophoresis was through 6% polyacrylamide-7M urea gels in Tris-borate buffer (pH 8.3) with a Sequi-Gen apparatus (Bio-Rad Laboratories, Richmond, Calif.), as described by the manufacturer. Gels were derived and exposed to Kodak XAK-5 film at room temperature. Primers used include the M13-40 and reverse primers (United States Biochemical) and synthetic 15-mer primers (Northern Biosciences, Hamel, Minn.). Sequence data were analyzed by the IntelliGenetics Suite of programs (release 6.01) and the PC/GENE program (release 5.35) (IntelliGenetics, Inc., Mountain View, Calif.). The facilities of the University of Minnesota Molecular Biology Computing Center were used to screen DNA data bases GenBank (release 61) and EMBL (release 20).

Figure 5:
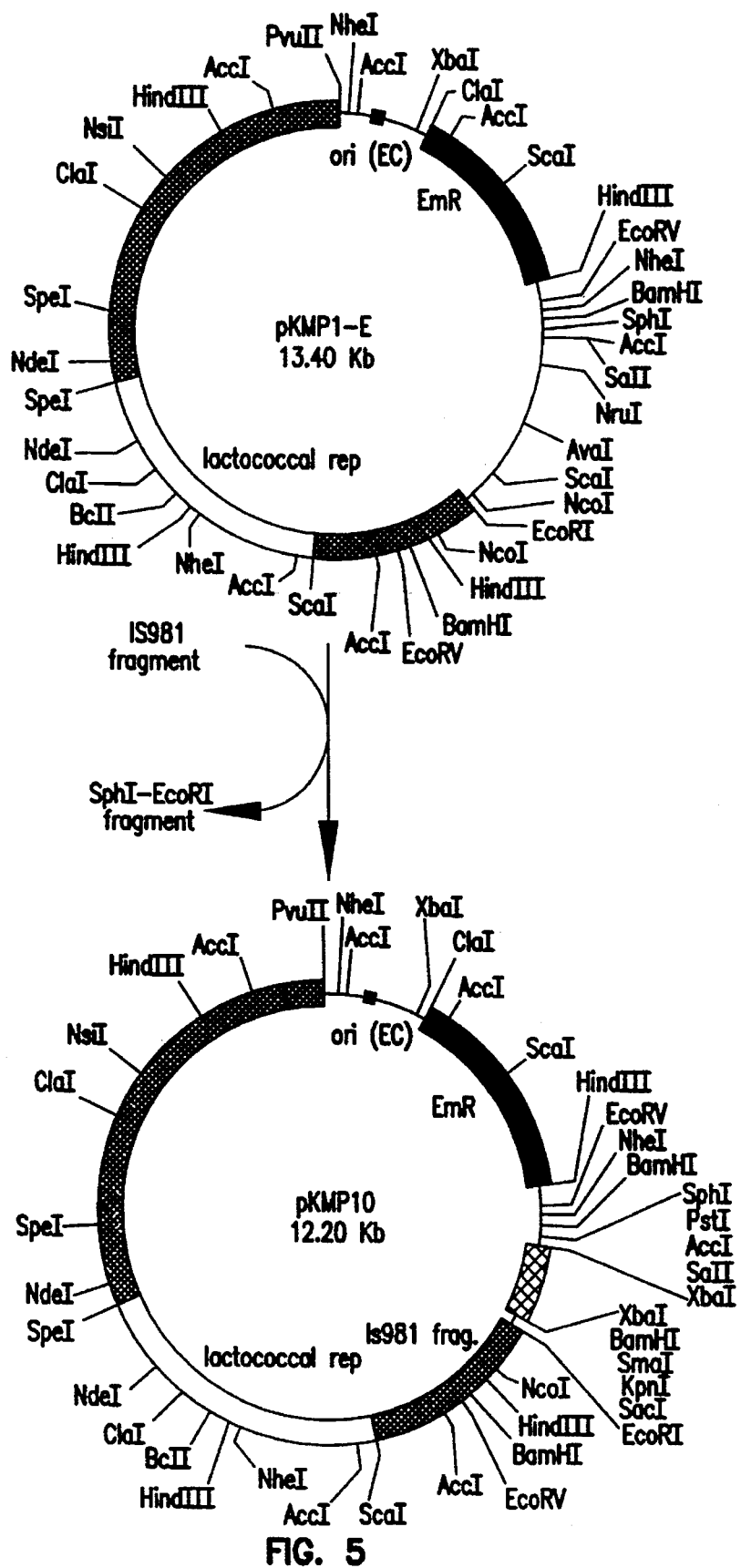
FIG. 5 represents construction of an integration vector (pKMP10) from pKMP1-E by replacement of a portion of pVA891 with the 0.7 kb XbaI fragment of IS981.

To determine the type of gene product conferring nisin resistance and its regulation the sequence of the 1.4-kb EcoR1-NdeI fragment from pLLM3 associated with nisin resistance was determined (FIG. 5). The 1.1-kb EcoR1-SacI fragment cloned in pBluescript SK(+) (pLLM6) was initially used to determine part of the DNA sequence. After the initial sequence determination, the majority of the EcoR1-KpnI fragment of pLLM3 was sequenced by using a cascade sequencing strategy with synthetic primers as reported by B. Froseth et al., *Appl. and Env. Micro.*, 57:804 (1991), which is hereby incorporated by reference. Both strands of a 1,454-bp fragment was sequenced and correspond to SEQ ID NO:3. The predicted amino acid sequence corresponds to SEQ ID NO:4. The total sequenced DNA included the entire EcoR1-NdeI fragment and 118 bp of the adjacent NdeI-KpnI fragment.

A single large open reading frame (ORF) was present. The ORF, designated nsr, was composed of 957 nucleotides and extended from an ATG start codon at position 354 to the frame-in-frame stop codon (TAA) at position 1310. The ORF has the potential to encode a protein of 35,035 Da comprising 318 amino acids.

EXAMPLE III

Identification of a Novel Lactococcal Insertion Sequence

1. Bacterial Strains and Plasmids

The *L. lactis* strains used in this study were pGBK17(pGBM17), an LM0230 transformant containing a 19-kb HpaII fragment of pKR223 which encodes a restriction-modification system and an abortive bacteriophage infection mechanism (Abi) cloned into pGB301 and MN14(pMN14), the pGBK17-derivative containing the DNA insertion which inactivated the abi gene(s). The *L. lactis* strains screened for the presence of IS981 were obtained from the laboratory stock culture collection. Strains GBK17 and MN14 were grown in M17 broth supplemented with 0.5% glucose and erythromycin (5 µg/ml). The *L. lactis* strains screened for the presence of IS981 were grown in M17 broth supplemented with 0.5% lactose, except for strains LM0230, MMS268, and MG1363 which were grown in M17 broth supplemented with 0.5% glucose. All cultures were grown at 32° C. pGBK17 and pMN14 restriction fragments were subcloned into the vectors pUC118 and pUC119(19) or pBluescript SK(+) and pBluescript SK(−) (Stratagene, La Jolla, Calif.). Transformation was into *Escherichia coli* XL-1 Blue (Stratagene). XL-1 Blue and Xl-1 Blue transformants were grown in LB broth (15) and LB broth supplemented with ampicillin (50 µg/ml), respectively, at 37° C. with shaking.

Plasmid isolation, restriction enzyme digestion, agarose gel electrophoresis, and cloning were conducted as described in Example 1. DNA sequencing and Sequence Analysis was conducted as described in Example 2.

2. Verification and Localization of the Insertion Sequence in the abi Genes of pGBK17 and DNA Sequence of the IS981

Figure 4:
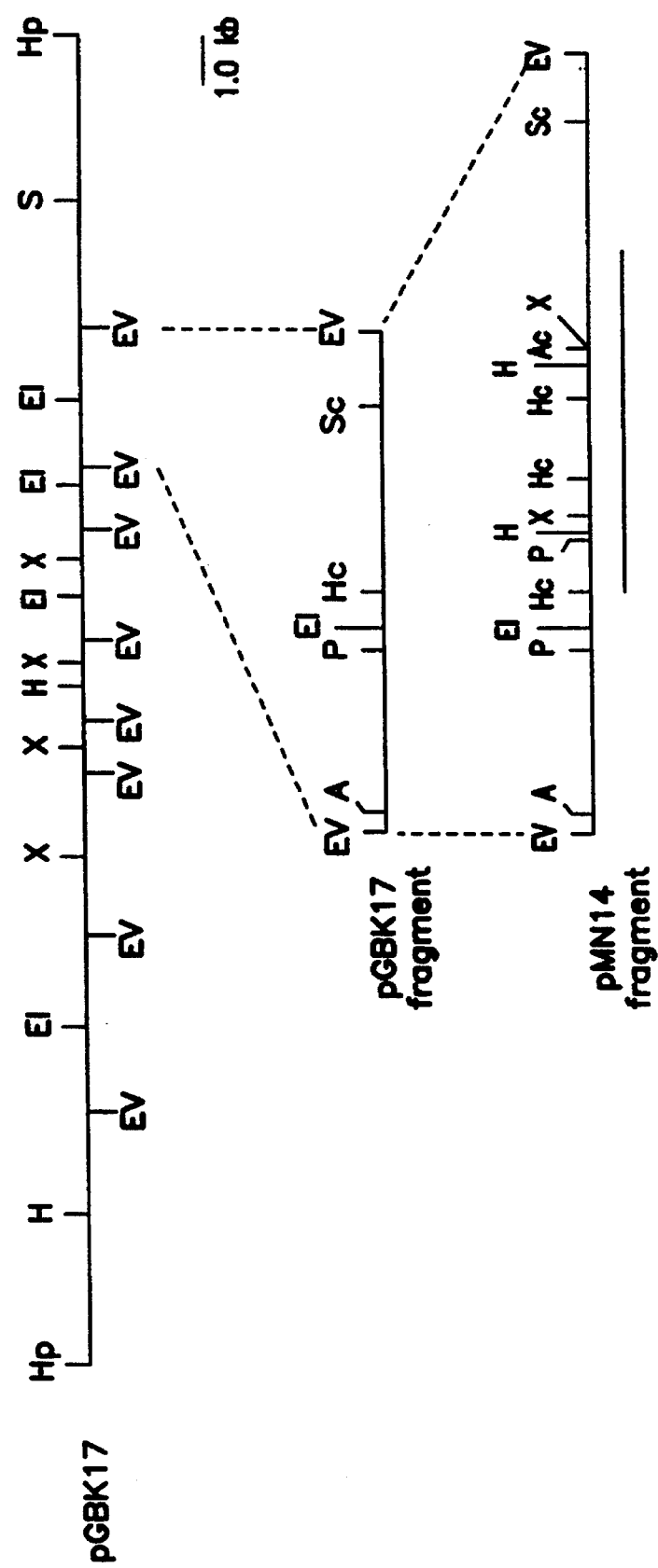
FIG. 4 represents the restriction maps of pGBK17, pGBK17 target fragment, and pMN14 insertion fragments.

As reported previously, initial restriction mapping of pMN14, the prolate-phage-sensitive derivative of pGMK17, suggested that pMN14 contained a 1.2- to 1.4-kb insertion within the 1.1-kb EcoRI-EcoRV fragment of the abi gene(s) of pGBK17. To confirm and further localize the insertion, the 2.0-kb EcoRV target fragment of pGBK17 and the corresponding 3.2-kb EcoRV insertion fragment of pMN14 were cloned into *E. coli* and detailed restriction maps were prepared. Although the 3.2-kb EcoRV insertion fragment contained several restriction sites in common with the 2.0-kb EcoRV target fragment, it contained additional restriction sites within its central region, confirming that the insertion fragment was derived from the target fragment but contained an insertion in its central region (FIG. 4). In addition, the more accurate sizing of the fragments during restriction mapping indicated that the insertion was about 1.2 kb in size. By comparing the restriction maps of the fragments, the region containing the additional DNA was located on pMN14 (FIG. 4). This insertion was tentatively named IS981.

The DNA sequences of both strands of the pGBK17 target fragment and the pMN14 insertion fragment were determined so that the limits of IS981 could be identified and its sequence could be examined for features characteristic of IS elements.

The ends of the insertion were determined by comparing the target and insertion fragment DNA sequences. The DNA sequences of the two fragments were identical from the common EcoRI sites through the region encoding ATATT, which ends at bp 240. After that sequence, however, the insertion fragment contained additional sequences not present in the target fragment. The target fragment DNA sequence immediately following bp 240 was again present in the insertion fragment DNA sequence starting at bp 1468. Therefore, IS981 was determined to begin with the GAT following the ATATT sequence and end with the GTC preceding another ATATT sequence. The 5-bp sequence of target DNA (ATATT) was duplicated at the insertion site, producing direct repeats flanking IS981. However, as only one insertion was available for sequencing, it could not be determined whether the actual direct repeat consisting of 4 bp, in which case the final T of the 5-bp direct repeat would actually be part of IS981.

The complete sequence of IS981 was determined and corresponds to SEQ ID NO:5. IS981 is 1,222 bp in size, as reported by K. Polzin et al., *Appl. Env. Micro.*, 57:734 (1991), which is hereby incorporated by reference. It did not contain perfect inverted repeats at its ends; however, an imperfect inverted repeat having 26 of 40 bp inverted was present. Examination of IS981 for open reading frames (ORFs) (<200 bp) revealed two potential ORFs, one extending from bp 58 to 318 (ORF1) and the other extending from bp 330 to 1169 (ORF2).

3. Examination of Lactococcus Species Chromosomal DNA for IS981

Total genomic DNA was prepared from nine *L. lactis* subsp. *lactis*, four *L. lactis* subsp. *lactis* biovar diacetylactis, six *L. lactis* subsp. *cremoris,* and five commercially used *L. lactis* strains. The *L. lactis* subsp. *lactis* DNAs were prepared as described by Ramos, *M. S. Thesis*, Univ. of Minn. (1989). The DNAs from the remaining strains were prepared by the same method, except that 0.5M sucrose-0.01M Tris (pH 7.0) buffer and 10 µl of mutanolysin (1 mg/ml in deionized distilled water) (Miles Laboratories, Elkhart, Ind.) were used instead of 25% glucose-10 mM Tris-1 mM EDTA (pH 7.0) buffer and 10 µl of lysozyme (10 mg/ml). After RNase A treatment, all DNAs were extracted once with phenol-chloroform-isoamyl alcohol (25:24:1) and once with chloroform-isoamyl alcohol (24:1), followed by ethanol precipitation. DNA was digested with HindIII for 7 to 16 h at 37° C. Electrophoresis was in a 0.6% agarose gel for either 5 h at 4 V/cm or 16 h at 1.4 V/cm in TAE buffer. Gels were stained in EtBr (0.5 µg/ml), and Southern transfers to Nytran membranes (Schleicher & Schuell, Keene, N. H.), prepared as described by the manufacturer. DNA labeling, hybridization, and detection were conducted by using the Genius Kit (Boehringer Mannheim, Indianapolis, Ind.), except that the probe labeling reaction was scaled to 50 µl as recommended in *BMBiochemica* (Boehringer Mannheim; November 1989). The probe was purified by ethanol precipitation with 7.5M ammonium acetate rather than 4M LiCl.

The IS981 insertion into pGBK17 was isolated following transformation of pGBK17 into the plasmid-free recipient strain, LM0230. Total DNA was isolated from LM0230 and plasmid DNA was isolated from GBK17 and MN14 to determine the source of IS981. The DNA was digested with either EcoRV or XbaI, and the digests were probed by Southern hybridization with the 0.7-kb XbaI fragment of IS981. The 0.7-kb probe fragment did not show significant hybridization to pGBK17 digested with EcoRV, confirming that IS981 did not originate from pGBK17. The fragment hybridized strongly to the 3.2-kb EcoRV and to the 0.7-kb XbaI fragments of pMN14 from which the probe fragment was derived. Finally, the probe hybridized to a 0.7-kp XbaI fragment of LM0230 chromosomal DNA, thus confirming that the LM0230 chromosome was the source of IS981.

The number of copies of IS981 present on the LM0230 chromosome was determined by isolating total LM0230 and MN14 DNA and GBK17 and MN14 plasmid DNA, digesting with HindIII, an enzyme which does not cut within IS981, and probing the digestions with the same 0.7-kb XbaI fragment. No significant hybridization to pGBK17 DNA was detected, while an approximately 17-kb HindIII fragment was detected in pMN14. However, at least 14 bands were detected in LM0230. Fourteen bands, including the band corresponding to the 17-kb HindIII plasmid band from pMN14, were also detected in MN14. The 14 bands detected in the HindIII digestion must all contain the 0.7-kb XabI fragment and, therefore, must contain closely related, if not identical, sequences to IS981 since only one band was detected in the XbaI digestion. Thus, LM0230 contains at least 14 IS981-like sequences in its chromosome.

Although MN14 is an LM0230 transformant, two of the bands detected in MN14 were not present in LM0230, and three of the bands in LM0230 were missing from MN14. This suggests that the positions of the IS981-like sequences are not fixed in the genome.

IS elements are often present in strains related to the strain from which they were isolated. To determine whether IS981 was present in other strains of lactococci, total DNA was isolated from *L. lactis* subsp. *lactis* LM0230 Miles LM0230, C2, MMS368, ML3, MG1363, 712, and 11454, *L. lactis* subsp. *lactis* bovar *diacetylactis* 11007, WM4, DPS, and 18-16, *L. lactis* subsp. *cremoris* C3, SK11, EBT, R1, Z8, and KH, and five commercially used *L. lactis* strains. The number of copies varied from 4 in C3 to 26 in SK11, including the faintly hybridizing upper bands, although it is possible that some of the faint bands are the result of partial digestion. Assuming that they are not, these numbers are only a minimum, as individual bands may contain more than one IS981-like sequence, and it was not determined whether some of the strongly hybridizing bands were actually multiple bands, high-copy number bands derived from plasmids, or simply regions of strong homology.

TABLE 1

Distribution of IS981 Sequences In Species of Lactococcus

| Bacterial Species | Number of Copies | Present In Chromosome |
| --- | --- | --- |
| *L. lactis* subsplactin | 7–15 | Yes |
| *L. Lactic* subsplactis biovar diacetylactis | 6–12 | Not Determined |
| *L. lactic* subsp. *cremoris* | 4–16 | Not Determined |
| Commercial starter strains | 13–25 | Not Determined |

As seen in Table 1, the *L. lactis* subsp. *lactis* strains contained seven (strain 11454) to 15 bands that hybridized to various degrees (strain ML3), the *L. lactis* subsp. *lactis* biovar diacetylactis strains contained 6 (strain 18-16) to 12 (strain WM4), the *L. lactis* subsp. *cremoris* strains contained 4 (strain C3) to 26 (strain SK11), and the commercial starter strains contained 13 (strain KR2) to 25 (strain KR1). It was also noted that, except for the commercial starter strains and the *L. lactis* subsp. *cremoris* C3, all strains of a given subspecies contained at least one band in common (e.g., the smallest band among the *L. lactis* subsp. *cremoris* strains and the smallest of the *L. lactis* subsp. *lactis* biovar diacetylactis bands). In addition, some strains within a subspecies contained many hybridizing bands in common, e.g., strains WM4 and 11007, and strains EB₇ and R1.

The results for *L. lactis* subsp. *lactis* provided additional information about these strains and about IS981. Strains C2 and LM0230, ML3, and MMS368, and 712 and MG1363 are pairs of plasmid-containing parent strains and their plasmid-free derivatives, respectively. The majority of hybridizing bands present in the plasmid-containing strains C2, ML3, and 712 were also present in their respective plasmid-free derivatives, LM0230, MMS368, and MG1363, indicating that most of the IS981-like sequences are present on the chromosome rather than on the plasmid DNA of these strains. It has not been determined whether those bands that differ between plasmid-containing and plasmid-free strains are due to different locations of IS981-like sequences on the chromosome or to plasmid copies of the sequences.

EXAMPLE IV

Development of a Lactococcal Integration Vector

1. Bacterial Strains and Plasmids

Plasmid-free *L. lactis* subsp. *lactis* strains were grown at 32° C. in M17 broth supplemented with 0.5% glucose (M17-G). Lactococcal transformants were grown at 25 or 32° C. in M17-G containing erythromycin (Em) 10 μg/ml). *E. coli* INV1αF' transformants were grown at 37° C. with shaking in LB broth supplemented with Em (30 μg/ml) or ampicillin (50 μg/ml). Frozen stocks of *L. lactis* subsp. *lactis* strains were prepared by mixing 1 ml of an overnight culture with 1 ml sterile reconstituted skim milk (11%) and stored at −65° C.

DNA isolation, restriction enzyme digestion, agarose gel electrophoresis and cloning were conducted as described in Example I.

2. Construction of Integration Vector pKMP10 pKMP10 has three components: the replication and temperature-sensitive maintenance regions from pSK11L, the Em$^R$ determinant and *E. coli* origin of replication from pVA891, and the internal 0.7-kb XbaI fragment of IS981 (FIG. 5). The pSK11L replication and temperature-sensitive maintenance regions had been cloned previously in pVA891 as described in Example 1 and localized to the 8.1-kb EcoR1-PvuII fragment of pSK11L cloned in pKMP1-E (FIG. 5). pKMP1-E, therefore, contained the pSK11L and pVA891 regions necessary for construction of pKMP10. To add the IS981 fragment to pKMP1-E, the 0.7-kb XbaI fragment obtained as described in Example 3 was first subcloned into the XbaI site in the polylinker of pSP73 to create pSP73(IS). pSP73(IS) and pKMP1-E were then digested with EcoR1 and SphI, mixed, ligated, and transformed into *E. coli* INV1αF'. Em$^R$ transformants were screened for plasmids in which the IS981 fragment plus some polylinker had replaced the 2.0-kb EcoR1-SphI fragment of pKMP1-E to form pKMP10. pKMP10 was capable of replication in both *E. coli* and lactococci, and contained unique PvuII, SphI, PstI, SalI, SmaI, KpnI, SacI, EcoR1, and NcoI sites. A unique NsiI site was also present; however, cloning into this site may affect plasmid stability and the percentage of the population containing integrated molecules.

3. Verification of pKMP10 temperature-sensitive maintenance in various *L. lactis* subsp. *lactis* strains pKMP10 was electroporated into *L. lactis* subsp. *lactis* LM0230, MG1363, and MMS368. These three strains were chosen because they are closely related and contain the same number of IS981-like sequences. pKMP10 stability in the lactococcal strains was determined by inoculating 25 μl of frozen stock into 9 ml M17-G containing Em and growing overnight at 25° C. Cultures were then diluted in M17-G to produce duplicate cultures of about 10³ CFU/ml. One culture was grown at 25° C. and the other at 39° C. Before and after growth, viable counts were determined (incubation at 30° C.), and 100 colonies were picked to M17-G plates containing Em. Plates were incubated at 30° C. and scored for the percentage of erythromycin resistant (Em$^R$) colonies. The percent loss per generation was determined using the equation from Roberts et al., *J. Bact.*, 172:6204 (1990).

$$\text{loss per generation} = 1 - \frac{F_i}{F_f} \times 100$$

where n is the number of generations elapsed, $F_i$ is the fraction of cells containing the plasmid at the initial time point, and $F_f$ is the fraction of cells containing the plasmid at the final time point.

Stability assays at 25° C. revealed that pKMP10 was less stable in LM0230 than was pKMP1-E at 25° C., indicating that replacement of the 2.0-kb EcoR1-SphI fragment of pVA891 with the IS sequence had slightly destabilized the plasmid in LM0230.

pKMP10 was equally unstable in MMS368 and LM0230 at 25° C., but was slightly more stable in MG1363 at this temperature. However, pKMP10 displayed the temperature-sensitive maintenance phenotype in all three host strains as indicated by the 3.5- to 15-fold increase in % loss/generation during growth at 39 as compared to 25° C.

4. Isolation of pKMP10 Integrants

A 25-μl sample from a frozen stock culture of LM0230(pKMP10) was inoculated into 9 ml M17-G containing Em (10 μg/ml) and grown overnight at 25° C. The culture was then diluted to 10³ CFU/ml (10⁻⁶ dilution) in M17-G broth either with or without Em and grown at 39° C. to stationary phase (24 h). Cultures not containing Em were then diluted to approximately 10⁴ CFU/ml in M17-G with Em and grown again at 39° C. to stationary phase (24 to 48 h). Cultures were plated on M17-G plates containing Em following each growth at 39° C. and incubated at 30° C. Twelve Em$^R$ colonies were inoculated into M17-G broth containing Em, grown overnight at 32° C., and screened for the presence of plasmid DNA.

No putative integrants (Em$^R$ colonies lacking plasmid DNA) were isolated following a single growth cycle at 39° C. regardless of whether the culture had been grown with or without Em. However, when LM0230(pKMP10) was grown first at 39° C. without Em to cure unintegrated pKMP10 and then at 39° C. with Em to further cure pKMP10 and to enrich for integrants, 8–75% (average of 56%) of the Em$^R$ colonies no longer contained detectable plasmid DNA which indicated that pKMP10 had integrated into the chromosome. Putative pKMP10 integrants were also isolated from MG1363(pKMP10) but at a ten-fold lower frequency.

Using the same procedure, no putative integrants were isolated from the Rec-deficient strain MMS368(pKMP10), as was expected if integration depended on homologous recombination. Also as expected, LM0230(pKMP1-E) did not yield any putative integrants presumably because it lacked the IS981 fragment required for integration.

5. Verification of pKMP10 Integration by Southern Hybridization

Seventeen putative integrants from two independent experiments were examined by Southern hybridization for evidence of pKMP10 integration. Total DNA was isolated from each strain, digested with ClaI and probed with the *E. coli* origin—erm gene fragment of pKMP10. If integration occurred by homologous recombination between plasmid and chromosomal IS981 sequences, this probe would detect one pKMP10 fragment and one of the junction fragments generated by the recombination event (a fragment distinct from the IS981-containing fragment of autonomous pKMP10). If the vector was not present or had not integrated, no fragment or only the original vector fragments would be detected, respectively. Of the 17 strains screened, 14 contained the pKMP10 fragment, a junction fragment of different sizes in different strains, and the pKMP10 IS981-containing ClaI fragment. Among these 14 integrants four differently sized junction fragments, suggestive of four different chromosomal insertion sites, were detected (classes i6, i7, i8, and i9). The remaining three putative integrants appeared to be identical, with each missing the pKMP10 IS981-containing ClaI band but containing the other pKMP10 fragment as well as a junction fragment distinct from those observed above (class i4). Thus five classes of integrants were identified.

The missing pKMP10 IS981-containing ClaI fragment in i4-class integrants indicated that a single copy of pKMP10 had integrated via homologous recombination somewhere within this fragment in these integrants. The retention of this fragment in the other four classes suggested that either integration had not occurred within this fragment in these integrants or pKMP10 had integrated as a tandem repeat structure resulting in regeneration of the pKMP10 IS981-containing fragment. To distinguish between these two possibilities total DNA from a representative of each of these four classes was digested with ScaI and probed with the ScaI-HindIII fragment of the erm gene of pKMP10. This probe would detect a junction fragment only if recombination occurred within the IS981-containing ScaI fragment. Probe 1 detected both a junction fragment having different sizes in each integrant as well as the original pKMP10 IS981-containing ScaI fragment in all four integrants. Comigration of this junction fragment with the pKMP10 fragment occurred. These results indicated that integration had occurred within the IS981-containing ScaI fragment, but that more than one pKMP10 molecule had integrated at the same chromosomal location in a tandem repeat structure.

The five integrant classes were screened for integration by homologous recombination with chromosomal IS981 sequences by probing total DNA with the 0.7-kb XbaI fragment of IS981. The Campbell model for integration predicts that if pKMP10 integrated by homologous recombination between its IS981 fragment and a chromosomal copy of IS981, a chromosomal IS981 band will be missing and two IS981-containing junction fragments will be present. During initial examinations it was determined that pKMP10 integration in the i4 class (which contained a single integrated copy of pKMP10), had not been by homologous recombination between vector and chromosomal IS981 sequences. The structure of this class was not examined further. The result of probing ScaI digents of the four classes with probe 2 show that each of the four integrant DNAs were clearly missing a different IS981 hybridizing band confirming that pKMP10 had integrated into a different chromosomal IS981 sequence in each integrant. Examination for putative junction fragments revealed two junction fragments in KMP10-i6 and KMP10-i9. However, in KMP10-i7 and KMP10-i8 only one junction fragment was clearly visible suggesting that the second junction fragment may be comigrating with LM0230 bands.

Comigration of the missing junction fragments with LM0230 bands was verified by probing ScaI-digested integrant DNAs with probe 1, which detected one of the two junction fragments, and ScaI digested LM0230 DNA from the same agarose gel with probe 2 to detect IS981-hybridizing bands. This allowed direct comparison of the migration of junction and LM0230 IS981 bands. Comparison of KMP10-i7 and KMP10-i8 DNAs probed with probe 1 with LM0230 probed with probe 2 showed that these integrants did contain a junction fragment that would comigrate with LM0230 IS981 bands c and d and bands n and o.

The model for Campbell-like integration requires that the sum of the sizes of the junction fragments be equal to the sum of the sizes of the missing chromosomal and pKMP10 IS981-containing bands. This was true for the four integrants examined. Therefore, all four integrants exhibited the missing fragment and two new junction fragments expected if pKMP10 integrated by Campbell-like homologous recombination between plasmid and chromosomal IS981 sequences.

6. Stability of pKMP10 Integration During Growth Without Selection

The five KMP10 integrants were examined for pKMP10 excision by growing for 100 generations without Em and then determining the percentage of $Em^S$ cells. While 100% of the cells from the strain containing unintegrated pKMP10 (KMP10-ul) had lost the plasmid, only KMP10-i4, which did not utilize IS981 for integration, showed detectable plasmid loss (2%); integrants in which pKMP10 integrated via IS981 showed no plasmid loss.

To verify that the four strains which integrated via IS981 still retained the plasmid in its integrated state following growth without selection, genomic DNA was isolated, digested with ScaI, and probed with probe 2. No decrease in the intensity of junction bands nor restoration of the missing chromosomal band indicative of pKMP10 excision, nor any other changes in the IS981 hybridization pattern were observed. Therefore, pKMP10 excision by homologous recombination of the IS981 repeats apparently did not occur at a detectable frequency. Retention of the IS981-containing pKMP10 band suggested that the tandem repeat structure of pKMP10 was stable even in the absence of selective pressure.

7. Replacement of the *E. coli* Origin of Replication and Erythromycin Resistance Gene in pKMP10 with a Lactococcal Food-Grade Marker By replacing the erythromycin resistance gene and *E. coli* origin of replication with a lactococcal marker gene, the pKMP10 vector would become food-grade and useful in industrial dairy fermentations involving lactococci, and possibly also in other lactic acid bacteria food fermentation processes.

The following approach was taken to replace the *E. coli* DNA fragment of pKMP10. First, a 1.8-kb restriction fragment encoding nisin resistance was subcloned into the EcoRI-KpnI site of pKMP10. The nisin resistance gene which is being used as a lactococcal food-grade marker was from pNP40, a plasmid discovered in our laboratory to encode nisin resistance as described in Example 2. The resulting integrative plasmid now contained the nisin resistance gene in addition to the regions mentioned above, i.e. the temperature sensitive replication region of lactococcal plasmid pSK11L, an internal fragment of IS981, and the erythromycin resistance gene and *E. coli* replication origin of pVA891. The second step is to delete the *E. coli* DNA fragment from pKMP10. This can be accomplished using routine molecular biology techniques which are described in T. Maniatis, *Molecular Cloning: A Laboratory Manual* (1982), which is hereby incorporated by reference, and will result in a food-grade vector consisting entirely of lactococcal DNA.

EXAMPLE 5

Incorporation of a Gene Encoding An Unstable Trait Into the Lactococcal Integration Vector Several traits are known to be unstable in species of bacteria important in industrial processes. One trait which can be lost or is unstable is the ability to ferment lactose. Lactose fermentation enzymes are encoded by a group of genes known as the lactose operon and are found on plasmids in Lactococcus species. The lactose operon can be isolated and cloned into the pKMP10 integration vector described in Example 4.

The lactose operon is found on the plasmid pSK11L with BclI. The 13 kbp BclI fragment encoding the lactose operon is isolated by subcloning. The lactose operon is then cloned into the lactococcal integration vector pKMP10 carrying nisin resistance gene by following standard recombinant DNA methods as described in T. Maniatis et al. *Molecular Cloning: A Laboratory Manual,* Cold Spring Harbor Laboratory (1982) which is hereby incorporated by reference. The BclI fragment encoding the lactose operon from pSK11L is isolated and subcloned into the site in the polylinker pSP73 as described in Example 4 for the insertion sequence IS981. The pSP73 and the pKMP10 are digested with restriction enzymes, mixed, ligated and transformed into *E. coli* LNVI2F'. Lactose fermenting and nisin resistant transformants are identified and are screened for plasmids containing the lactose operon.

These plasmids are further characterized and selected so that the plasmids selected replicate in Lactococcal species in a temperature sensitive manner, encode a gene for nisin resistance, encode at least one insertion sequence, and carry the lactose operon. Plasmids with these characteristics are electroporated into Lactococcus species, which are then grown at 37° C. to enrich for bacteria with integrated plasmids as described in Example 4.

What is claimed is:

1. An integration vector to be integrated into a microorganism's chromosome comprising as operably joined components:

(a) a first DNA sequence, wherein said first DNA sequence encodes a plasmid replication and maintenance sequence from plasmid pSK11, wherein the plasmid replication or maintenance sequence provides for temperature sensitive loss of the autonomously replicating plasmid and wherein said sequence includes at least a 2.3 kb ScaI-SpeI fragment; and (b) a second DNA sequence, wherein said second DNA sequence is comprised of at least one selectable food grade marker gene; and (c) a third DNA sequence, wherein said third DNA sequence encodes a fragment of an insertion sequence, and wherein said fragment of the insertion sequence has sufficient sequence identity to DNA sequences on the microorganism's chromosome to provide for integration of the vector into the chromosome by homologous recombination, wherein the microorganism is selected from the group consisting of Pediococcus, Leuconostoc, Lactococcus, Lactobacillus, *Streptococcus thermophilous,* and Bacillus; and (d) a fourth DNA sequence, wherein said fourth DNA sequence is comprised of at least one gene encoding an unstable trait.

2. The integration vector of claim 1, wherein said integration vector has DNA sequences that correspond to DNA sequences present in bacteria of the Genus Lactococcus.

3. The integration vector of claim 1, wherein the food-grade marker gene is selected from the group of genes consisting of nisin resistance genes, β-galactosidase gene, lactose metabolism genes, sucrose metabolism genes, bacteriophage resistance genes, bacteriocin resistance and immunity genes and mixtures thereof.

4. The integration vector according to claim 1, wherein said insertion sequence in said third DNA sequence has sufficient sequence identity to DNA sequences on a chromosome of Lactococcus species of bacteria to provide for integration of the vector into the chromosome by homologous recombination.

5. The integration vector according to claim 4, wherein the fragment of an insertion sequence corresponds to insertion sequence IS981 or portions thereof including at least 700 base pairs.

6. The integration vector of claim 1, wherein said gene encoding an unstable trait of said fourth DNA sequence is selected from the group consisting of lactose metabolism genes, proteinase genes, citrate metabolism genes, bacteriocin production and immunity genes, nisin resistance genes, exopolymer genes, bacteriophage resistance genes, and mixtures thereof.

7. The integration vector of claim 1, which comprises less than about 100 kilobase pairs.

8. A integration vector according to claim 1, wherein autonomous replication of the integration vector is inhibited at a temperature of at least about 37° C.

9. An integration vector according to claim 1, wherein the first DNA sequence corresponds to the 2.3 kilobase pair ScaI-SpeI fragment of the 14.8 kilobase pair PvuII fragment of the pSK11L plasmid.

10. A DNA sequence according to claim 9 corresponding to the second open reading frame and the upstream noncoding ori sequences on the 2.3 kilobase pair ScaI-SpeI fragment (SEQ ID NO:1) of pSK11L.

11. An integration vector according to claim 1, wherein the second DNA sequence corresponds to 1.454 kilobase EcoRI-NdeI fragment from pLLM3 encoding a nisin resistance gene (SEQ ID NO:3).

12. A DNA sequence corresponding to the insertion sequence IS981 (SEQ ID NO:5) and portions thereof including at least 700 base pairs.

13. A DNA sequence according to claim 12, corresponding to the 700 base pair XbaI restriction fragment of insertion sequence IS981.

14. A DNA sequence corresponding to the 14.8 kilobase pair PvuII fragment of the pSK11L plasmid and portions thereof including at least a 2.3 kb ScaI-SpeI fragment.

15. A DNA sequence according to claim 14 corresponding to a 1.2 kilobase pair ClaI-HindIII fragment of the 14.8 kilobase pair fragment PvuII fragment of the psK11L plasmid.

16. A method of increasing the stability of inheritance of genes encoding traits in a microorganism by integration of the genes into a microorganism's chromosome comprising the steps of:

(a) introducing an integration vector into a microorganism, wherein said integration vector is comprised as operably joined components a first DNA sequence wherein said first DNA sequence encodes a plasmid replication and maintenance sequence from pSK11, wherein the plasmid replication or maintenance sequence provides for temperature sensitive loss of the autonomously replicating plasmid, and wherein said sequence includes at least a 2.3 kb ScaI-SpeI fragment;

a second DNA sequence, wherein said second DNA sequence is comprised of at least one food grade selectable marker gene; a third DNA sequence, wherein said third DNA sequence encodes a fragment of an insertion sequence, and wherein said fragment of the insertion sequence has sufficient sequence identity to DNA sequences on a bacterial chromosome to provide for integration of the vector into the chromosome by homologous recombination, wherein the bacteria is selected from the group consisting of Pediococcus Leuconostoc, Lactococcus Lactobacillus, *Streptococcus thermophilous,* and Bacillus; and a fourth DNA sequence, wherein said fourth DNA sequence is comprised of at least one gene encoding an unstable trait to yield a transformed population of microorganisms; and (b) subjecting the population of transformed microorganisms to a selective condition to yield a selected population of microorganisms; and (c) growing the selected population of microorganisms through a plurality of growth cycles to confirm that a population of microorganisms exhibits an increase in the stability of inheritance of a gene encoding an unstable trait is obtained.

17. A method according to claim 16, wherein the integration vector is introduced into a population of microorganisms by electroporation, protoplast transformation, transduction, or liposomal encapsulation.

18. The method according to claim 16, wherein the selective condition is comprised of conducting a growth cycle of transformed population of microorganisms at a temperature effective to inhibit temperature sensitive autonomous replication of the integration vector followed by conducting a growth cycle of the transformed population of microorganisms at an effective temperature to inhibit the replication of the integration vector and in the presence of an effective amount of a selective agent.

19. A method according to claim 18, wherein the effective temperature is at least about 37° C.

20. The method according to claim 16, wherein the plurality of growth cycles is at least about 50–100 generations.

21. A method according to claim 16, further comprising selecting microorganisms which exhibit expression of the selectable marker gene and lack autonomously replicating integration vector DNA.

22. A transformed microorganism which exhibits an increase in the stability of the inheritance of a gene encoding an unstable trait, wherein said microorganism has an integration vector integrated into a chromosome, and wherein said integration vector is comprised as operably joined components:

a first DNA sequence, wherein said first DNA sequence encodes a plasmid replication and maintenance sequence from pSK11, wherein the plasmid replication or maintenance sequence provides for temperature sensitive loss of the autonomously replicating plasmids, wherein said sequence includes at least a 2.3 kb ScaI-SpeI fragment;

a second DNA sequence, wherein said second DNA sequence is comprised of at least one selectable food grade marker gene;

a third DNA sequence, wherein said third DNA sequence encodes a fragment of an insertion sequence and wherein said fragment of the insertion sequence has sufficient sequence identity to DNA sequences on a microorganism chromosome to provide for integration of the vector into the chromosome by homologous recombination, wherein the microorganism is selected from the group consisting of Pediococcus, Leuconostoc, Lactococcus, Lactobacillus, *Streptococcus thermophilous,* and Bacillus; and a fourth DNA sequence, wherein said fourth DNA sequence is comprised of at least one gene encoding an unstable trait.

23. The microorganism of claim 22, wherein the integration vector is comprised of DNA sequences which correspond to DNA sequences present in bacteria of the Genus Lactococcus.

24. The microorganism of claim 22, wherein the microorganism is a bacteria of the Genus Lactococcus.

25. The microorganism of claim 22, having the characteristics of ATCC No. 68917.

26. An integration vector to be integrated into a microorganism's chromosome comprising as operably joined components:

(a) a first DNA sequence, wherein said first DNA sequence encodes a plasmid replication and maintenance sequence from pSK11, wherein the plasmid replication or maintenance sequence provides for temperature sensitive loss of the autonomously replicating plasmid and wherein said sequence includes at least a 2.3 kb ScaI-SpeI fragment; and (b) a second DNA sequence, wherein said second DNA sequence is comprised of at least one food grade selectable marker gene; and (c) a third DNA sequence, wherein said third DNA sequence encodes a fragment of a lactococcal insertion sequence IS981, and wherein said fragment of the insertion sequence has sufficient sequence identity to DNA sequences on the lactococcal bacterial chromosome to provide for integration of the vector into the chromosome by homologous recombination, wherein the bacteria is a Lactococcal species; and (d) a fourth DNA sequence, wherein said fourth DNA sequence encodes an unstable trait selected from the group consisting of lactose metabolism genes, proteinase genes, citrate metabolism genes, bacteriocin production and immunity genes, nisin resistance genes, exopolymer genes, and bacteriophage resistance genes.

27. The integration vector of claim 26, wherein the food grade marker gene is selected from the group of genes consisting of nisin resistance genes, $\beta$-galactosidase gene, lactose metabolism genes, sucrose metabolism genes, bacteriophage resistance genes, bacteriocin resistance and immunity genes and mixtures thereof.

28. An integration vector according to claim 26, wherein autonomous replication of the integration vector is inhibited at a temperature of at least about 37° C.

* * * * *

UNITED STATES PATENT AND TRADEMARK OFFICE
CERTIFICATE OF CORRECTION

PATENT NO. : 5,459,072

DATED : October 17, 1995

INVENTOR(S) : Larry L. McKay et al.

It is certified that error appears in the above-identified patent and that said Letters Patent is hereby corrected as shown below:

At column 7, line 10, for "Microorqanism" read --Microorganism--

At column 14, line 45, for "Microorqanism" read --Microorganism--

At column 22, line 11, for "(pKMPi-X)" read --(pKMP1-X)--

At column 22, line 28, for "EB5" read --EB$_5$--

At column 25, line 29, for "(<200 bp)" read --(>200 bp)--

At column 26, line 36, for "EBT" read --EB$_7$--

Signed and Sealed this

Twenty-sixth Day of March, 1996

Attest:

BRUCE LEHMAN

Attesting Officer

Commissioner of Patents and Trademarks